US009868961B2

(12) United States Patent
Allison et al.

(10) Patent No.: US 9,868,961 B2
(45) Date of Patent: Jan. 16, 2018

(54) METHODS AND COMPOSITIONS FOR LOCALIZED SECRETION OF ANTI-CTLA-4 ANTIBODIES

(75) Inventors: James Allison, New York, NY (US); Michael Curran, New York, NY (US)

(73) Assignee: The Regents of the University of California, Oakland, CA (US)

( * ) Notice: Subject to any disclaimer, the term of this patent is extended or adjusted under 35 U.S.C. 154(b) by 2097 days.

(21) Appl. No.: 12/294,889

(22) PCT Filed: Mar. 30, 2007

(86) PCT No.: PCT/US2007/007983
§ 371 (c)(1),
(2), (4) Date: Oct. 29, 2010

(87) PCT Pub. No.: WO2007/123737
PCT Pub. Date: Nov. 1, 2007

(65) Prior Publication Data
US 2011/0044953 A1 Feb. 24, 2011
US 2017/0114364 A9 Apr. 27, 2017

Related U.S. Application Data

(60) Provisional application No. 60/787,972, filed on Mar. 30, 2006, provisional application No. 60/787,978, filed on Mar. 31, 2006.

(51) Int. Cl.
C12N 15/86 (2006.01)

(52) U.S. Cl.
CPC .................................. C12N 15/86 (2013.01)

(58) Field of Classification Search
None
See application file for complete search history.

(56) References Cited

U.S. PATENT DOCUMENTS

| | | | |
|---|---|---|---|
| 5,078,996 A | 1/1992 | Conlon, III et al. | |
| 5,098,702 A | 3/1992 | Zimmerman et al. | |
| 5,436,146 A | 7/1995 | Shenk et al. | |
| 5,543,328 A | 8/1996 | McClelland et al. | |
| 5,637,483 A | 6/1997 | Dranoff et al. | |
| 5,686,279 A | 11/1997 | Finer et al. | |
| 5,731,190 A | 3/1998 | Wickham et al. | |
| 5,753,500 A | 5/1998 | Shenk et al. | |
| 5,756,086 A | 5/1998 | McClelland et al. | |
| 5,770,442 A | 6/1998 | Wickham et al. | |
| 5,811,097 A * | 9/1998 | Allison et al. | 424/144.1 |
| 5,846,767 A | 12/1998 | Halpin et al. | |
| 5,846,782 A | 12/1998 | Wickham et al. | |
| 5,904,920 A | 5/1999 | Dranoff et al. | |
| 5,922,315 A | 7/1999 | Roy | |
| 5,935,821 A | 8/1999 | Chatterjee et al. | |
| 5,985,290 A | 11/1999 | Jaffee et al. | |
| 6,033,674 A | 3/2000 | Jaffee et al. | |
| 6,040,183 A | 3/2000 | Ferrari et al. | |
| 6,057,155 A | 5/2000 | Wickham et al. | |
| 6,093,570 A | 7/2000 | Ferrari et al. | |
| 6,117,425 A | 9/2000 | MacPhee et al. | |
| 6,127,525 A | 10/2000 | Crystal et al. | |
| 6,187,306 B1 | 2/2001 | Pardoll et al. | |
| 6,331,415 B1 | 12/2001 | Cabilly et al. | |
| 6,350,445 B1 | 2/2002 | Jaffee et al. | |
| 6,464,973 B1 | 10/2002 | Levitsky et al. | |
| 6,548,286 B1 | 4/2003 | Samulski et al. | |
| 6,555,368 B1 | 4/2003 | Curiel | |
| 6,602,503 B1 | 8/2003 | Lobb et al. | |
| 6,623,940 B1 | 9/2003 | Ledbetter et al. | |
| 6,683,170 B2 | 1/2004 | Curiel et al. | |
| 6,692,736 B2 | 2/2004 | Yu et al. | |
| 6,984,720 B1 | 1/2006 | Korman et al. | |
| 7,034,121 B2 | 4/2006 | Carreno et al. | |
| 7,256,037 B2 | 8/2007 | Ellenhorn et al. | |
| 7,485,291 B2 | 2/2009 | Fang et al. | |
| 7,592,007 B2 | 9/2009 | Gribben et al. | |
| 7,919,079 B2 * | 4/2011 | Simmons et al. | 424/93.21 |
| 8,106,092 B2 | 1/2012 | Ogbourne et al. | |
| 2002/0039581 A1 * | 4/2002 | Carreno et al. | 424/178.1 |
| 2002/0168342 A1 | 11/2002 | Wang et al. | |
| 2004/0202650 A1 * | 10/2004 | Gribben et al. | 424/131.1 |
| 2004/0208850 A1 * | 10/2004 | Ellenhorn et al. | 424/93.2 |
| 2005/0002916 A1 | 1/2005 | Jooss et al. | |
| 2008/0014222 A1 * | 1/2008 | Simmons et al. | 424/277.1 |
| 2008/0187513 A1 * | 8/2008 | Ogbourne et al. | 424/85.2 |

FOREIGN PATENT DOCUMENTS

| | | |
|---|---|---|
| CA | 2648067 A3 | 11/2007 |
| EP | 2002263 B1 | 6/2014 |
| WO | WO 97/16209 A1 | 5/1997 |
| WO | WO 99/39734 A1 | 8/1999 |
| WO | WO 99/42585 A1 | 8/1999 |
| WO | WO 00/37504 A2 | 6/2000 |

(Continued)

OTHER PUBLICATIONS

Souza et al. (Brazilian Journal of Medical and Biological Research (2005) 38: 509-522).*
van Elsas et al., 1999 J Exp Med 190:355-366.*
Akiyama et al., "Enhancement of antitumor immunity against B16 melaneoma tumor using genetically modified denditic cells to produce cytokines." Gene Therapy, vol. 7, pp. 2113-2121 (2000).
Allison, "Blockade of T cell inhibitory signals: a new paradigm in tumor immunotherapy?" Cancer Immun. vol. 5(1), p. 9 (2005).
Altschul et al., "Basic local alignment search tool." J. Mol. Biol.vol. 215(3), pp. 403-410 (1990).
Aoki et al., "Expression of murine interleukin 7 in a murine glioma cell line results in reduced tumorigenicity in vivo." PNAS vol. 89(9), pp. 3850-3854 (1992).
Armstrong et al., "Cytokine modified tumor vaccines." Surg. Oncol. Clin. N. Am. vol. 11(3), pp. 681-696 (2002).
Attia et al., "Autoimmunity correlates with tumor regression in patients with metastatic melanoma treated with anti-cytotoxic T-lymphocyte antigen-4." Clin. Oncol. vol. 23(25), pp. 6043-6053 (2005).
Barber, et al., "Restoring function in exhausted CD8 T cells during chronic viral infection." Nature vol. 439(7077), pp. 682-687 (2006).

(Continued)

Primary Examiner — Ilia Ouspenski
(74) Attorney, Agent, or Firm — Todd A. Lorenz

(57) ABSTRACT

The present invention provides compositions and methods for effectuating the localized expression of anti-CTLA-4 antibody proximal to a target tissue in a patient.

14 Claims, 14 Drawing Sheets

(56) References Cited

FOREIGN PATENT DOCUMENTS

| WO | WO 00/67576 A1 | 11/2000 |
|---|---|---|
| WO | WO 00/72686 A1 | 12/2000 |
| WO | WO 01/54732 A1 | 8/2001 |
| WO | WO 03/066810 A2 | 8/2003 |
| WO | WO 2004/058801 A2 | 7/2004 |
| WO | WO 2004/093831 A2 | 11/2004 |
| WO | WO 2004/113493 A2 | 12/2004 |
| WO | WO 2005/003298 A2 | 1/2005 |
| WO | WO 2005/017149 A1 | 2/2005 |
| WO | WO 2005/027966 A2 | 3/2005 |

OTHER PUBLICATIONS

Batzer et al., "Enhanced evolutionar PCR using oligonucleotides with inosine at the 3'-terminus." Nucleic Acids Res. vol. 19(18), p. 5081 (1991).

Bett et al., "Packaging capacity and stability of human adenovius type 5 vectors." J. Virol. vol. 67(10), pp. 5911-5921 (1993).

Bluestone et al., "CTLA4Ig: bridging the basic immunology with clinical application." Immunity vol. 24(3), pp. 233-238 (2006).

Bodey et al., "Failure of cancer aaccines: the significant limitations of this approach to immunotherapy." Anticancer Res. vol. 20(4), pp. 2665-2676 (2000).

Bossis and Chiorini, "Cloning of an avian adeno-associated virus (AAAV) and generation of recombinant AAAV particles." J. Virol. vol. 77(12), pp. 6799-6810 (2003).

Brunner et al., "CTLA-4-mediated inhibition of early events of T cell proliferation." J. Immunol. vol. 162(10), pp. 5813-5820 (1999).

Chambers et al., "CTLA-4-mediated inhibition in regulation of T cell responses: mechanisms and manipulation in tumor immunotherapy." Annu. Rev. Immunol. vol. 19, pp. 565-594 (2001).

Chang et al., "Immunogenetic therapy of human melanoma utilizing autologous tumor cells transduced to secrete granulocyte-macrophage colony-stimulating factor." Human Gene Therapy vol. 11, pp. 839-850 (2000).

Chaplin et al., "Production of interleukin-12 as a self-processing 2A polypeptide." J. Interferon Cytokine Res. vol. 19(3), pp. 235-241 (1999).

Chu and Sharp, "SV40 DNA transfection of cells in suspension: analysis of the efficiency of transcription and translation of T-antigen." Gene.vol. 13(2), pp. 197-202 (1981).

Chumsae et al., "Identification and localization of unpaired cysteine residues in monoclonal antibodies by florescence labeling and mass spectrometry." Anal. Chem. vol. 81, pp. 6449-6457 (2009).

Darrow et al., "The role of HLA class I antigens in recognition of melanoma cells by tumor-specific cytotoxic T lymphocytes. evidence for shared tumor antigens." J. Immunol. vol. 142(9), pp. 3329-3335 (1989).

de Felipe and Izquierdo, "Tricistronic and tetracistronic retroviral vectors for gene transfer." Hum. Gene Ther. vol. 11(13), pp. 1921-1931 (2000).

de Felipe et al., "Use of the 2A sequence from foot-and-mouth disease virus in the generation of retroviral vectors for gene therapy." Gene Ther. vol. 6(2), pp. 198-208 (1999).

Donnelly et al., "Analysis of the aphthovirus 2A/2B polyprotein 'cleavage' mechanism indicates not a proteolytic reaction, but a novel translational effect : a putative ribosomal 'skip'." J. Gen. Virol.vol. 82(5), pp. 1013-1025 (2001).

Donnelly et al., "The 'cleavage' activities of foot-and-mouth disease virus 2A site-directed mutants and naturally occurring '2A-like' sequences." J. Gen. Virol. vol. 82(5), pp. 1027-1041 (2001).

Dranoff et al., "Vaccination with irradiated tumor cells engineered to secrete murine granulocyte-macrophage colony-stimulating factor stimulates potent, specific, and long-lasting anti-tumor immunity." PNAS vol. 90(8), pp. 3539-3543 (1993).

Dull et al., "A third-generation lentivirus vector with a conditional packaging system." J Virol. vol. 72(11), pp. 8463-8471 (1998).

Dummer, "GVAX (Cell Genesys)." Curr Opin Investig Drugs. vol. 2(6), pp. 844-848 (2001).

Emens et al., "A phase I vaccine safety and chemotherapy dose-finding trial of an allogeneic GM-CSF-secreting breast cancer vaccine given in a specifically timed sequence with immunomodulatory doses of cyclophosphamide and doxorubicin." Hum. Gene Ther. vol. 15(3), pp. 313-337 (2004).

Fearon et al., "Interleukin-2 production by tumor cells bypasses T helper function in the generation of an antitumor response." Cell vol. 60(3), pp. 397-403 (1990).

Fields Virology, 3rd Edition, editied by B.N. Fields et al., Lippincott Raven Publishers, ch. 58, "Retrovidae: the viruses and their relication," Classification, pp. 1768-1777, including Table 1 (1996).

Finer et al., "*kat*: a high-efficiency retroviral transduction system for primary human T lymphocytes." Blood vol. 83(1), pp. 43-50 (1994).

Gansbacher et al., "Interleukin 2 gene transfer into tumor cells bbrogates tumorigenicity and induces protective immunity." J. Exp. Med. vol. 172(4), pp. 1217-1224 (1990).

Gansbacher et al., "Retroviral vector-mediated gamma-interferon gene transfer into tumor cells generates potent and long lasting antitumor immunity." Cancer Res. vol. 50(24), pp. 7820-7825 (1990).

Gao et al., "Adeno-associated viruses undergo substantial evolution in primates during natural infections." PNAS vol. 100(10), pp. 6081-6086 (2003).

Gao et al., "Novel adeno-associated viruses from rhesus monkeys as vectors for human gene therapy." PNAS vol. 99(18), pp. 11854-11859 (2003).

Golumbeck et al., "Treatment of established renal cancer of tumor cells engineer to secrete interleukin-4." Science vol. 254(5032), pp. 713-716 (1991).

Graham et al., "A new technique for the assay of infectivity of human adenovirus 5 DNA". Virology vol. 52(2), pp. 456-467 (1973).

Greenwald et al., "The B7 family revisited." Ann. Rev. Immunol. vol. 23, pp. 515-548 (2005).

Griffin et al., "Development and applications of surface-linked single chain antibodies against T-cell antigens.", J. Immunol. Methods, vol. 248 (1-2) pp. 77-90 (2001).

Halpin et al., "Self-processing 2A-polyproteins—a system for coordinate expression of multiple proteins in transgenic plants." Plant J. vol. 17(4), pp. 453-459 (1999).

Hartley and Rowe, "Naturally occurring murine leukemia viruses in wild mice: characterization of a new 'amphotropic' class." J Virol. vol. 19(1), pp. 19-25 (1976).

Hock et al., "Interleukin 7 induces CD4 + T cell-dependent tumor rejection." J. Exp. Med. vol. 174(6), pp. 1291-1298 (1991).

Hodi et al., "Biologic activity of cytotoxic T lymphocyte-associated antigen 4 antibody blockade in previously vaccinated mestatic melanoma and ovarian carcinoma patients," PNAS, vol. 100, pp. 4712-4717 (2003).

Hom et al., "Common expression of melanoma tumor-associated antigens recognized by human tumor infiltrating lymphocytes: analysis by human lymphocytes antigen restriction." J Immunother. vol. 10(3), pp. 153-164 (1991).

Huang et al., "Role of bone marrow-derived cells in presenting MHC class I-restricted tumor antigens." Science vol. 264(5161), pp. 961-965 (1994).

Huez et al., "Two independent internal ribosome entry sites are involved in translation initiation of vascular endothelial growth factor mRNA." Mol Cell Biol. vol. 18(11), pp. 6178-6190 (1998).

Jackson and Kaminski, "Internal initiation of translation in eukaryotes: the picornavirus paradigm and beyond." RNA vol. 1(10), pp. 985-1000 (1995).

Jackson et al., "The novel mechanism of initiation of picornavirus RNA translation." Trends Biochem. Sci. vol. 15(12), pp. 477-483 (1990).

Jaffee and Pardoll, "Gene therapy: its potential applications in the treatment of renal-cell carcinoma." Semin Oncol. vol. 22(1), pp. 81-91 (1995).

Jaffee et al., "Clinical protocal: a phase I clinical trial of lethally irradiated allogeneic pancreatic tumor cells transfected with the GM-CSF gene for the treatment of pancreatic adenorcarcinoma." Hum. Gene Ther. vol. 9 (13), pp. 1951-1971 (1998).

(56) References Cited

OTHER PUBLICATIONS

Jaffee et al., "Development and characterization of a cytokine-secreting pancreatic adenocarcinoma vaccine from primary tumors for use in clinical trials." Cancer J. Sci. Am. vol. 4(3), pp. 194-203 (1998).
Jaffee et al., "Novel allogeneic granulocyte-macrophage colony-stimulating factor-secreting tumor vaccine forpancreatic cancer: a phase I trial of safety and immune activation." J. Clin. Oncol. vol. 19(1), pp. 145-156 (2001).
Kawakami et al., "Shared human melanoma antigens: Recognition by tumor-infiltrating lymphocytes in HLA-A2.I-transfected melanomas." J. Immunol. vol. 148(2), pp. 638-643 (1992).
Klein et al., "Properties of the K562 cell line, derived from a patient with chronic myeloid leukemia." Int. J. Cancer vol. 18(4), pp. 421-431 (1976).
Kohler and Milstein, "Derivation of specific antibody-producing tissue culture and tumor lines by cell fusion." Eur. J. Immunol. vol. 6(7), pp. 511-519 (1976).
Korman et al., "Tumor immunotherapy: preclinical and clinical activity of anti-CTLA4 antibodies." Curr. Opin. Investig. Drugs vol. 6(6), pp. 582-591 (2005).
Leach, et al. "Enhancement of antitumor immunity by CTLA-4 blockade." Science vol. 271, pp. 1734-1736 (1996).
Lee et al., "Genetic immunotherapy of established tumors with adenovirus-murine granulocyte-macrophage colony-stimulating factor." Hum. Gene Ther. vol. 8(2), pp. 187-193 (1997).
Londrigan et al. "Prolonged local expression of anti-CD4 antibody by adenovially transduced allografts can promote long-term graft survival." J. Gene Medicine vol. 8(1), pp. 42-52 (2006).
Lyerly, "Quantitating cellular immune tesponses to cancer vaccines." Semin. Oncol. vol. 30(3 Suppl 8), pp. 9-16 (2003).
McCarty et al., "Self-complementary recombinant adeno associated virus (scAAV) vectors promote efficient transduction independently of DNA synthesis." Gene Ther. vol. 8(16), pp. 1248-1254 (2001).
Miller, "Human gene therapy comes of age." Nature vol. 357(6378), pp. 455-460 (1992).
Miyazaki et al., "Expression vector system based on the chicken beta-actin promoter directs efficient production of interleukin-5." Gene vol. 79(2), pp. 269-277 (1989).
Mulligan and Berg, "Expression of a bacterial gene in mammalian cells." Science vol. 209(4463), pp. 1422-1427 (1980).
Nagai et al., "Irradiated tumor cells adenovirally engineered to secrete granulocyte/macrophage-colony-stimulating factor establish antitumor immunity and eliminate pre-existing tumors in syngeneic mice." Cancer Immunol. Immunother. vol. 47(2), pp. 72-80 (1998).
Needleman and Wunsch, "A general method applicable to the search for similarities in the amino acid sequence of two proteins." J. Mol. Biol. vol. 48(3), pp. 443-453 (1970).
Nemunaitis et al., "Granulocyte—macrophage colony-stimulating factor gene-modified autologous tumor vaccines in non—small-cell lung cancer." J. Natl. Cancer Inst. vol. 96(4), pp. 326-331 (2004).
Oettgen et al., "The history of cancer immunotherapy." Biologic Therapy of Cancer, ch. 6, pp. 87-119 (1991).
Ohtsuka et al., "An alternative approach to deoxyoligonucleotides as hybridization probes by insertion of deoxyinosine at ambiguous codon positions." J Biol Chem. vol. 260(5), pp. 2605-2608 (1985).
Ono et al., "Production of anti-prion scFv-FC fusion proteins by recombinant animal cells." J. Biosci.. Bioeng. vol. 95(3), pp. 231-238 (2003).
Ory et al., "A stable human-derived packaging cell line for production of high titer retrovirus/vesicular stomatitis virus G pseudotypes." PNAS vol. 93(21), pp. 11400-11406 (1996).
Palmenberg, "Proteolytic processing of picornaviral polyprotein." Annu. Rev. Microbiol. vol. 44, pp. 603-623 (1990).
Pearson and Lipman, "Improved tools for biological sequence comparison." PNAS vol. 85(8), pp. 2444-2448 (1988).
Peggs et al. "Principles and use of anti-CTLA4 antibody in human cancer immunotherapy." Curr. Opin. Immunol. vol. 18(2), pp. 206-213 (2006).
Perreau and Kremer, "Frequency, proliferation, and activation of human memory T cells induced by a nonhuman adenovirus." J. Virol. vol. 79(23), pp. 14606-14613 (2005).
Phan et al., "Cancer regression and autoimmunity induced by cytotoxic T lymphocyte-associated antigen 4 blockade in patients with metastatic melanoma." PNAS vol. 100(14), pp. 8372-8377 (2003).
Pistillo, et al. "Anti-CTLA-4 human scFv antibodies prevent T-cell activation in transplantation." Trans. Proceedings vol. 33(1-2), pp. 285-287 (2001).
Porgador et al., "Immunotherapy of tumor metastasis via gene therapy." Nat. Immun. vol. 13(2-3), pp. 113-130 (1994).
Ribas et al., "Genetically modified dendritic cells for cancer immunotherapy," Current Gene Therapy, vol. 5 (6), pp. 619-628 (2005).
Ribas et al., "Immunosuppressive effects of interleukin-12 coexpression in melanoma antigen gene-modified dendritic cell vaccines." Cancer Gene Therapy vol. 9, pp. 875-883 (2002).
Roosien et al., "Synthesis of foot-and-mouth disease virus capsid proteins in insect cells using baculovirus expression vectors." J. Gen. Virol. vol. 71 (Pt 8), pp. 1703-1711 (1990).
Rossolini et al., "Use of deoxyinosine-containing primers vs degenerate primers for polymerase chain reaction based on ambiguous sequence information." Mol. Cell Probes. vol. 8(2), pp. 91-98 (1994).
Ryan and Drew, "Foot-and-mouth disease virus 2A oligopeptide mediated cleavage of an artificial polyprotein." EMBO J. vol. 13(4), pp. 928-933 (1994).
Ryan et al., "Cleavage of foot-and-mouth disease virus polyprotein is mediated by residues located within a 19 amino acid sequence." J. Gen. Virol. vol. 72(Pt 11), pp. 2727-2732 (1991).
Ryan et al., "Specificity of enzyme-substrate interactions in foot-and-mouth disease virus polyprotein processing." Virology vol. 173(1), pp. 35-45 (1989).
Salgia et al., "Vaccination with irradiated autologous tumor cells engineered to secrete granulocyte-macrophage colony-stimulating factor augments antitumor immunity in somepatients with metastatic non-small-cell lung carcinoma." J. Clin. Oncol. vol. 21(4), pp. 624-630 (2003).
Sanderson et al., "Autoimmunity in a phase I trial of a fully human anti-cytotoxic t-lymphocyte antigen-4 monoclonal antibody with multiple melanoma peptides and montanide isa 51 for patients with resected stages iii and iv melanoma." J. Clin. Oncol. vol. 23(4), pp. 741-750 (2005).
Shi et al., "Granulocyte-macrophage colony-stimulating factor (GM-CSF) secreted by cDNA-transfected tumor cells induces a more potent antitumor response than exogenous GM-CSF.", Cancer Gene Therapy vol. 6 (1), pp. 81-88 (1999).
Simmons et al., "Local secretion of anit-CTLA4 antibody from a GM-CSF-secreting tumor cell vaccine enhances vaccine efficacy." Proceedings of the American Association for Cancer Research Annual Meeting, vol. 47, p. 359 (2006).
Simons et al., "Bioactivity of autologous irradiated renal cell carcinoma vaccines generated by ex vivo granulocyte-macrophage colony-stimulating factor gene transfer." Cancer Res. vol. 57(8), pp. 1537-1546 (1997).
Simons et al., "Induction of immunity to prostate cancer antigens: results of a clinical trial of vaccination with irradiated autologous prostate tumor cells engineered to secrete granulocyte-macrophage colony-stimulating factor using ex vivo gene transfer." Cancer Res. vol. 59(20), pp. 5160-5168 (1999).
Smith and Waterman, "Comparison of biosequences." Adv. Appl. Math., vol. 2(4), pp. 482-489 (1981).
Smith et al., "Localized expression of an anti-TNF single-chain antibody prevents development of callagen-induced arthritis." Gene Therapy vol. 10(15) pp. 1248-1257 (2003).
Soiffer et al., "Vaccination with irradiated autologous melanoma cells engineered to secrete human granulocyte-macrophage colony-stimulating factor generates potent antitumor immunity in patients with metastatic melanoma." PNAS vol. 95(22), pp. 13141-13146 (1998).

(56) References Cited

OTHER PUBLICATIONS

Soiffer et al., "Vaccination with irradiated, autologous melanoma cells engineered to secrete granulocyte-macrophage colony-stimulating factor by adenoviral-mediated gene transfer augments antitumor immunity in patients with metastatic melanoma." J. Clin. Oncol. vol. 21(17), pp. 3343-3350 (2003).

Souza et al., "Recombinant viruses as vaccines against viral diseases." Brazilian J. Med. Bio. Research vol. 38(4), pp. 509-522 (2005).

Sugden et al., "A vector that replicates as a plasmid and can be efficiently selected in b-lymphoblasts transformed by epstein-barr virus." Mol. Cell. Biol. vol. 5(2), pp. 410-413 (1985).

Szymczak et al., "Correction of multi-gene deficiency in vivo using a single 'self-cleaving' 2A peptide-based retroviral vector." Nat. Biotechnol. vol. 22(5), pp. 589-594 (2004).

Teng, et al., "Long-term inhibition of tumor growth by tumor necrosis factor in the absence of cachexia or T-cell immunity." PNAS vol. 88(9), pp. 3535-3539 (1991).

van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation." J. Exp. Med. vol. 190(3), pp. 355-366 (1999).

Wu et al. "Multimerization of a chimeric anti-CD20 single-chain Fv-Fc fusion protein is mediated through variable domain exchange." Prot. Eng. vol. 14(12), pp. 1025-1033 (2001).

Zennou et al., HIV-1 genome nuclear import is mediated by a central DNA flap. Cell vol. 101(2), pp. 173-185 (2000).

Zheng et al., "B7-CTLA4 interaction enhances both production of antitumor cytotoxic T lymphocytes and resistance to tumor challenge.", PNAS vol. 95 (11), pp. 6284-6289 (1998).

Zufferey et al., Self-inactivating lentivirus vector for safe and efficient in vivo gene delivery. J. Virol. vol. 72(12), pp. 9873-9880 (1998).

* cited by examiner

Light Chain:
- 5' Mk-FR1: 5'-gat atc agg cgc gcc GAY ATT GTG MTS ACM CAR WCT MCA – 3'
- 3' Kc: 5-gct ccc tcc gcc act tcc gcc acc act ccc acc tcc gga tcc GGA TAC AGT TGG TGC AGC ATC – 3'

Heavy Chain:
- 5' MHI-FR1: 5'-gga tcc gga ggt ggg agt ggt ggc gga agt ggc gga ggg agc SAR GTN MAG CTG SAG SAG TC – 3'
- 5' MH2-FR1: 5'- gga tcc gga ggt ggg agt ggt ggc gga agt ggc gga ggg agc SAR GTN MAG CTG SAG SAG TCW GG – 3'
- 3' IgG2B: 5'- c tcg aga aga tct AGG GGC CAG TGG ATA GAC TGA TGG

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      primer 5'Mk-FR1 Light chain

<400> SEQUENCE: 2
gatatcaggc gcgccgayat tgtgmtsacm carwctmca                               39

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence: Synthetic
      primer 3' Kc Light chain

<400> SEQUENCE: 3
gctccctccg ccacttccgc caccactccc acctccggat ccggatacag ttggtgcagc        60
atc                                                                     63

<210> SEQ ID NO 4
<211> LENGTH: 62
<212> TYPE: DNA
<213> ORGANISM: Artificial Sequence
<220> FEATURE:
<223> OTHER INFORMATION: Description of Artificial Sequence: Synthetic
      primer 5' MHI-FR1 Heavy Chain
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: misc_feature
<222> LOCATION: (48)..(48)
<223> OTHER INFORMATION: n is a, c, g, or t

<400> SEQUENCE: 4
ggatccggag gtgggagtgg tggcggaagt ggcggaggga gcsargtnma gctgsagsag        60
tc                                                                      62

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic
      primer 5'MH2-FR1 Heavy Chain
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: misc_feature
<222> LOCATION: (48)..(48)
<223> OTHER INFORMATION: n is a, c, g, or t

<400> SEQUENCE: 5
ggatccggag gtgggagtgg tggcggaagt ggcggaggga gcsargtnma gctgsagsag        60 tcwgg                                                                   65

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer 3' IgG2B Heavy Chain
```

```
<400> SEQUENCE: 6
ctcgagaaga tctaggggcc agtggataga ctgatgg                              37

<210> SEQ ID NO 7
<211> LENGTH: 823
<212> TYPE: DNA
<213> ORGANISM: Artificial Sequence
<220> FEATURE:
<223> OTHER INFORMATION: Description of Artificial Sequence: Synthetic
      polynucleotide 9D9 scFv molecule
<220> FEATURE:
<221> NAME/KEY: CDS
<222> LOCATION: (1)..(822)

<400> SEQUENCE: 7 gat atc agg cgc gcc gac att gtg atg acc cag act aca ctt tcc ctg      48
Asp Ile Arg Arg Ala Asp Ile Val Met Thr Gln Thr Thr Leu Ser Leu
1               5                   10                  15 cct gtc agt ctt gga gat caa gcc tcc atc tct tgc aga tct agt cag     96
Pro Val Ser Leu Gly Asp Gln Ala Ser Ile Ser Cys Arg Ser Ser Gln
            20                  25                  30 agc att gta cat agt aat gga aac acc tat tta gaa tgg tac ctg cag    144
Ser Ile Val His Ser Asn Gly Asn Thr Tyr Leu Glu Trp Tyr Leu Gln
        35                  40                  45 aaa cca ggc cag tct cca aag ctc ctg atc tac aaa gtt tcc aac cga    192
Lys Pro Gly Gln Ser Pro Lys Leu Leu Ile Tyr Lys Val Ser Asn Arg
    50                  55                  60 ttt tct ggg gtc cca gac agg ttc agt ggc agt gga tca ggg aca gat    240
Phe Ser Gly Val Pro Asp Arg Phe Ser Gly Ser Gly Ser Gly Thr Asp
65                  70                  75                  80 ttc aca ctc aag atc agc aga gtg gag gct gag gat ctg gga gtt tat    288
Phe Thr Leu Lys Ile Ser Arg Val Glu Ala Glu Asp Leu Gly Val Tyr
                85                  90                  95 tac tgc ttt caa ggt tca cat gtt cct tac acg ttc gga ggg ggg acc    336
Tyr Cys Phe Gln Gly Ser His Val Pro Tyr Thr Phe Gly Gly Gly Thr
            100                 105                 110 aag ctg gaa ata aaa cgg gct gat gct gca cca act gta tcc gga tcc    384
Lys Leu Glu Ile Lys Arg Ala Asp Ala Ala Pro Thr Val Ser Gly Ser
        115                 120                 125 gga ggt ggg agt ggt ggc gga agt ggc gga ggg agc gag gca aag ctg    432
Gly Gly Gly Ser Gly Gly Gly Ser Gly Gly Gly Ser Glu Ala Lys Leu
    130                 135                 140 cag gag tct gga cct gtg ctg gtg aag cct ggg gct tca gtg aag atg    480
Gln Glu Ser Gly Pro Val Leu Val Lys Pro Gly Ala Ser Val Lys Met
145                 150                 155                 160 tcc tgt aag gct tct gga tac aca ttc act gac tac tat atg aac tgg    528
Ser Cys Lys Ala Ser Gly Tyr Thr Phe Thr Asp Tyr Tyr Met Asn Trp
                165                 170                 175 gtg aag caa agc cat gga aag agc ctt gag tgg att gga gtt att aat    576
Val Lys Gln Ser His Gly Lys Ser Leu Glu Trp Ile Gly Val Ile Asn
            180                 185                 190 cct tat aac ggt gat act agc tac aac cag aag ttc aag ggc aag gcc    624
Pro Tyr Asn Gly Asp Thr Ser Tyr Asn Gln Lys Phe Lys Gly Lys Ala
        195                 200                 205 aca ttg act gtt gac aag tcc tcc agc aca gcc tac atg gag ctc aac    672
Thr Leu Thr Val Asp Lys Ser Ser Ser Thr Ala Tyr Met Glu Leu Asn
    210                 215                 220 agc ctg aca tct gag gac tct gca gtc tat tac tgt gca aga tac tat    720
Ser Leu Thr Ser Glu Asp Ser Ala Val Tyr Tyr Cys Ala Arg Tyr Tyr
225                 230                 235                 240 ggt tcc tgg ttt gct tac tgg ggc caa ggg act ctg atc act gtc tct    768
```

```
Gly Ser Trp Phe Ala Tyr Trp Gly Gln Gly Thr Leu Ile Thr Val Ser
            245                 250                 255 aca gcc aaa aca aca ccc cca tca gtc tat cca ctg gcc cct aga tct      816
Thr Ala Lys Thr Thr Pro Pro Ser Val Tyr Pro Leu Ala Pro Arg Ser
            260                 265                 270 tct cga g                                                             823
Ser Arg <210> SEQ ID NO 8
<211> LENGTH: 274
<212> TYPE: PRT
<213> ORGANISM: Artificial Sequence
<220> FEATURE:
<223> OTHER INFORMATION: Synthetic Construct

<400> SEQUENCE: 8

Asp Ile Arg Arg Ala Asp Ile Val Met Thr Gln Thr Thr Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
            35                  40                  45

Lys Pro Gly Gln Ser Pro Lys Leu Leu Ile Tyr Lys Val Ser Asn Arg
        50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Tyr Thr Phe Gly Gly Gly Thr
            100                 105                 110

Lys Leu Glu Ile Lys Arg Ala Asp Ala Ala Pro Thr Val Ser Gly Ser
            115                 120                 125

Gly Gly Gly Ser Gly Gly Gly Ser Gly Gly Gly Ser Glu Ala Lys Leu
        130                 135                 140

Gln Glu Ser Gly Pro Val Leu Val Lys Pro Gly Ala Ser Val Lys Met
145                 150                 155                 160

Ser Cys Lys Ala Ser Gly Tyr Thr Phe Thr Asp Tyr Tyr Met Asn Trp
                165                 170                 175

Val Lys Gln Ser His Gly Lys Ser Leu Glu Trp Ile Gly Val Ile Asn
            180                 185                 190

Pro Tyr Asn Gly Asp Thr Ser Tyr Asn Gln Lys Phe Lys Gly Lys Ala
        195                 200                 205

Thr Leu Thr Val Asp Lys Ser Ser Ser Thr Ala Tyr Met Glu Leu Asn
210                 215                 220

Ser Leu Thr Ser Glu Asp Ser Ala Val Tyr Tyr Cys Ala Arg Tyr Tyr
225                 230                 235                 240

Gly Ser Trp Phe Ala Tyr Trp Gly Gln Gly Thr Leu Ile Thr Val Ser
            245                 250                 255

Thr Ala Lys Thr Thr Pro Pro Ser Val Tyr Pro Leu Ala Pro Arg Ser
            260                 265                 270

Ser Arg
```

METHODS AND COMPOSITIONS FOR LOCALIZED SECRETION OF ANTI-CTLA-4 ANTIBODIES

CROSS REFERENCE TO RELATED APPLICATIONS

This is the National Stage filed under 35 U.S.C. §371 of International Application PCT/US2007/007983 filed on Mar. 30, 2007, which designated the United States of America, the disclosure of which is incorporated herein by reference. The present application claims priority from U.S. Provisional Patent Application No. 60/787,972 filed on 30 Mar. 2006, and U.S. Provisional Patent Application No. 60/787,978 filed on 31 Mar. 2006, the contents each of which are incorporated herein by reference.

The disclosure claims benefit under 35 U.S.C. §119(e) of U.S. Provisional Application Ser. No. 60/787,972 filed Mar. 30, 2006, and U.S. Provisional Application Ser. No. 60/787,987 filed Mar. 31, 2006, each of which is incorporated herein by reference in its entirety.

REFERENCE TO A SEQUENCE LISTING

A Sequence Listing is provided in this patent document as a txt file entitled "187609US3_ST25.txt" and created Sep. 30, 2010 (size 10 Kb). The contents of this file is incorporated herein by reference in its entirety.

FIELD OF THE INVENTION

The disclosure relates to methods and compositions for the localized secretion of anti-CTLA-4 antibodies and their use in immunotherapy.

BACKGROUND

Cytotoxic T lymphocyte antigen-4 (CTLA-4) is a member of the CD28-B7 immunoglobulin superfamily of immune regulatory molecules. Greenwald et al., *Ann. Rev. Immunol.* 23:515-548 (2005). Although initially mischaracterized as a positive regulator based on homology to its co-stimulatory counterpart CD28, CTLA-4 has now been recognized as one of the key negative regulators of adaptive immune responses in general, and T cell proliferation and effector functions in particular. Peggs et al., *Curr. Opin. Immunol.* 18:206-213 (2006). Unlike constitutively-expressed CD28, CTLA-4 expression is tightly regulated and short-lived on activated T cells, and exhibits significantly higher affinities for the B7 ligands it shares with CD28.

A number of clinical efforts are underway to therapeutically exploit the important biological function of this molecule. On the one hand, CTLA-4Ig fusion molecules have been created and employed as immune suppressants in vivo based on its higher affinity for B7 and the consequent inhibition of CD28-B7 mediated costimulation. Bluestone et al., *Immunity* 24:233-38 (2006). The hCTLA-Ig fusion protein Orencia™ (abatacept) recently received FDA approval as a first-in-class antagonist of CD28 costimulation in rheumatoid arthritis.

On the other hand, CTLA-4 blockade is being explored as a promising approach to cancer immunotherapy, employing monoclonal antibodies directed against CTLA-4 to prevent its negative regulation and thereby enhance the cellular immune response. Peggs, supra. Ongoing clinical investigations utilizing systemic administration of these antibodies have provided dramatic successes, but have also produced undesirable toxicities. In particular, adverse immune events (AIE) such as immune-mediated colitis, hypophysitis, uveitis and hepatitis have been observed, and serious AIE often correlate with antitumor responses or freedom from relapse. Attia at al., *J. Clin. Oncol.* 23:6043-53 (2005). Accordingly, although the current systemic approach may be clinically acceptable in a patient population having advanced disease and very limited treatment options, further improvement is clearly warranted to dissociate the positive anti-tumor effect from the negative adverse events.

SUMMARY OF THE INVENTION

The present invention resolves this unmet need in the art by effectuating localized CTLA-4 blockade in vivo, such that the distribution and effect of the desired CTLA-4 blockade is substantially restricted to a particular target tissue. More specifically, cells, viral vectors, compositions and methods are provided for the localized, in vivo secretion of anti-CTLA-4 antibodies from in vivo modified endogenous cells or ex vivo modified autologous or allogeneic cellular vaccines that are subsequently administered.

In one aspect, the invention provides a viral vector encoding an anti-CTLA-4 antibody (Ab) that binds to the extracellular domain of CTLA-4 and inhibits CTLA-4 signaling. In preferred embodiments for ex vivo transformation, the viral vector can be an integrative viral vector capable of providing constitutive expression when transfected into a human cell such as, e.g., adeno-associated viral (AAV) vectors and lentiviral vectors. In preferred embodiments for in vivo transformation, the viral vector can be a non-integrative viral vector capable of providing transient expression when transfected into a human cell such as, e.g., an adenoviral vector or an alpha virus vector. In certain preferred embodiments, the vector is an alpha virus vector selected from the group consisting of an SFV and an VEE vector.

The vector can further include a nucleic acid encoding a cytokine. In preferred embodiments, the cytokine is GM-CSF.

In another aspect, the invention provides a modified human cell expressing an anti-CTLA-4 antibody that specifically binds to the extracellular domain of CTLA-4 and inhibits CTLA-4 signaling. Preferably, the modified human cell is capable of expressing the anti-CTLA-4 antibody proximal to a tumor cell in a cancer patient in need thereof. In one embodiment, the cell is an endogenous cell modified in vivo in a patient to effectuate localized expression of anti-CTLA-4 antibody in a target tissue. In an alternative embodiment, the human cell is an autologous or allogeneic cell modified ex vivo to effectuate localized expression of anti-CTLA-4 antibody upon administration to a target tissue. In a preferred embodiment, the target tissue is tumor tissue.

In a further embodiment, the human cell is further modified to secrete at least one additional immune effector molecule such as, e.g., G-CSF, GM-CSF, IL-2 and the like.

In preferred embodiments, human cells suitable for modification in accordance with the invention include tumor cells, T cells and antigen-presenting cells such as, e.g., dendritic cells. Such cells may be endogenous and/or autologous to the patient for personalized cellular therapies, or allogeneic as in the case of cell line-derived cancer vaccines. In a preferred embodiment, cells administered in accordance with the invention will be rendered short-lived by any of the various methods well known in the art, such as, e.g., irradiation.

In preferred embodiments, anti-CTLA-4 antibodies will bind to the extracellular domain of CTLA-4, and may advantageously be full length antibodies as well as fragments thereof including, e.g., Fab fragments, Fd fragments, Fv fragments, F(ab')$_2$ fragments, bivalent fragments comprising two linked Fab fragments and/or single chain Fv fragments. In a particularly preferred embodiment, the anti-CTLA-4 antibody is an scFv fragment.

In preferred embodiments, the anti-CTLA-4 antibodies demonstrate reduced effector function. For example, the anti-CTLA-4 antibody can have reduced binding to Fc receptors. In certain variations, the anti-CTLA-4 antibody lacks an Fc region. In other variations, the anti-CTLA-4 antibody has all or part of an Fc region, but is engineered to have reduced Fc binding. In still other variations, the anti-CTLA-4 antibody can be engineered to have reduced dimerization, thereby reducing the capacity for ADCC effects.

Therapeutic compositions comprising human cells in the case of ex vivo manipulation, and expression vectors in the case of in vivo manipulation, are also provided. Suitable formulations as appropriate depending on the nature of the therapeutic composition are also contemplated.

In one aspect, methods for expressing an anti-CTLA-4 antibody proximal to a target tissue in a patient are provided, comprising transforming a human cell with an anti-CTLA-4 expression vector to express an anti-CTLA-4 antibody proximal to a target tissue. In accordance with the subject methods, the human cell may be transformed ex vivo and subsequently administered proximal to a target tissue in a patient. Alternatively, the human cell may be transformed in vivo. The human cell that is transformed in vivo to express anti-CTLA-4 Ab is preferably a tumor cell or a tumor-associated cell, such as a support cell situated proximal to a tumor cell, or an antigen-presenting cell (APC) (e.g. a dendritic cell). In each instance, anti-CTLA-4 antibody is expressed by the transformed cell and inhibits CTLA-4 mediated negative regulation in T cells proximal to a tumor cell.

In one embodiment, the anti-CTLA-4 expression vector used is a viral vector. In a preferred embodiment, the viral vector is selected from the group consisting of retroviral vectors, adeno-associated viral (AAV) vectors, adenoviral vectors, lentiviral vectors, and alpha virus vectors. In another embodiment, the anti-CTLA-4 expression vector is a non-viral vector.

In one embodiment, an anti-CTLA-4 expression vector comprises an anti-CTLA-4 Ab encoding nucleotide sequence operably linked to an expression control region which, taken together, may be integrated into the genome of the transformed human cell. In a preferred embodiment, such vectors are viral vectors. In a preferred embodiment, such viral vectors are selected from the group consisting of retroviral vectors, lentiviral vectors, and AAV vectors. In a preferred embodiment, such viral vectors are used for the stable transformation of human cells ex vivo.

In another embodiment, the anti-CTLA-4 expression vector comprises an anti-CTLA-4 Ab encoding nucleotide sequence that remains extrachromosomal in the transformed human cell. In a preferred embodiment, the anti-CTLA-4 expression vector is a viral vector selected from the group consisting of adenoviral vectors and alpha virus vectors, more preferably an alpha virus vector, and still more preferably an SFV or VEE vector. In a preferred embodiment, such viral vectors are used for the transient expression of anti-CTLA-4 antibodies in vivo in a transformed human cell.

In a preferred embodiment, the anti-CTLA-4 expression vector provides for high level, transient expression of anti-CTLA-4 Ab in the transformed human cell. High level transient expression is achievable, for example, with a SFV anti-CTLA-4 Ab viral vector.

In one aspect, the invention provides pharmaceutical compositions for local delivery to solid tumors that are useful for inhibiting the growth of solid tumors.

In one embodiment, the pharmaceutical composition comprises a non-viral anti-CTLA-4 expression vector and a gene delivery agent.

In a preferred embodiment, the pharmaceutical composition comprises a viral anti-CTLA-4 expression vector.

In one embodiment, the pharmaceutical compositions comprise a modified human cell capable of expressing an anti-CTLA-4 antibody.

In one aspect, the invention provides pharmaceutical compositions for local delivery to solid tumors that are useful for increasing the anti-tumor T cell response directed against the solid tumor.

In one embodiment, the pharmaceutical composition comprises a non-viral anti-CTLA-4 Ab expression vector and a gene delivery agent.

In a preferred embodiment, the pharmaceutical composition comprises a viral anti-CTLA-4 Ab expression vector.

In one embodiment, the pharmaceutical compositions comprise a modified human cell capable of expressing an anti-CTLA-4 antibody.

In one aspect, the invention provides pharmaceutical compositions for local delivery to solid tumors that are useful for the treatment of patients having solid tumors.

In one embodiment, the pharmaceutical composition comprises a non-viral anti-CTLA-4 Ab expression vector and a gene delivery agent.

In a preferred embodiment, the pharmaceutical composition comprises a viral anti-CTLA-4 Ab expression vector.

In one embodiment, the pharmaceutical compositions comprise a modified human cell capable of expressing an anti-CTLA-4 antibody.

In a further aspect, the modified human cell is administered to a patient. In certain embodiments, administration of the cell to the patient can be systemic, intramuscular or subcutaneous, or at the site of a tumor cell vaccination. In other embodiments, the cell can be administered at or proximal to the tumor site. In still other embodiments, the cell can be administered at or proximal to one or more lymph nodes of the patient.

In an additional aspect, the invention provides methods for producing a medicament useful for the treatment of a patient having a tumor, such as a solid tumor.

BRIEF DESCRIPTION OF THE DRAWINGS

FIG. 2 depicts the sequences of the light and heavy chain primers used in constructing the 9D9 antibody. The primer sequence of 5'Mk-FR1 Light Chain is set forth as SEQ ID NO:2. The primer sequence of 3' Kc Light Chain is set forth as SEQ ID NO:3. The primer sequence of 5'MHI-FR1 Heavy Chain is set forth as SEQ ID NO:4. The primer sequence of 5'MH2-FR1 Heavy Chain is set forth as SEQ ID NO:5. The primer sequence of 3' IgG2B Heavy Chain is set forth as SEQ ID NO:5.

FIG. 4 depicts the 9D9 scFv sequence. The nucleic acid sequence of 9D9 scFv is set forth as SEQ ID NO:7. The amino acid sequence of 9D9 scFv is set forth as SEQ ID NO:8.

DETAILED DESCRIPTION

Figure 1:
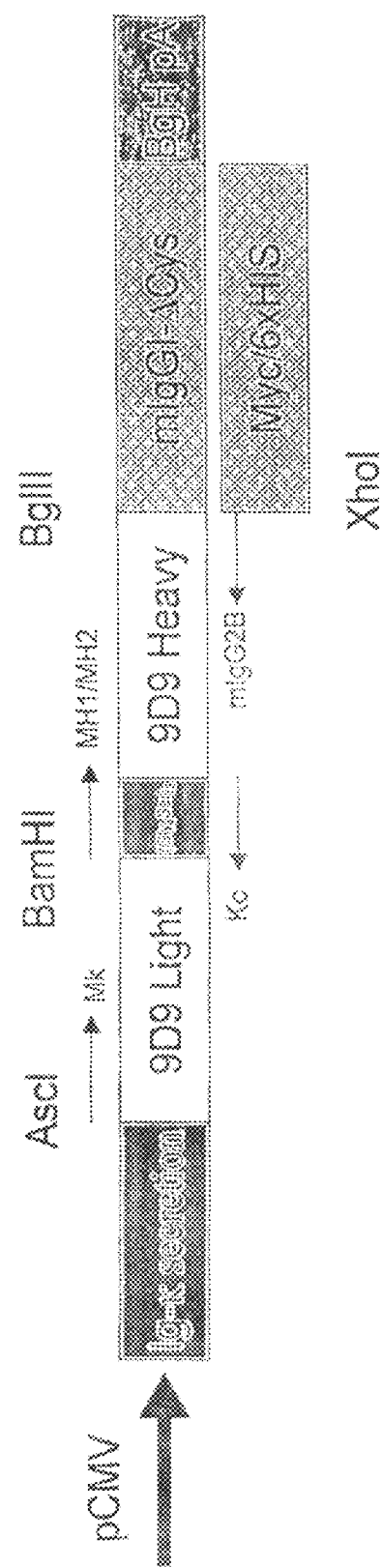
FIG. 1 depicts the cloning strategy for producing the 9D9 antibody.

The viral vectors and transformed human cells of the present invention express anti-CTLA-4 antibodies that inhibit CTLA-4 mediated negative signaling. In a preferred embodiment, the viral vector or human cells expressing the anti-CTLA-4 antibody are capable of expressing the antibody proximal to a tumor.

Human cells that can be used include tumor cells, antigen-presenting cells (e.g. dendritic cells), B cells and T cells. The presently disclosed cells provide for localized expression of anti-CTLA-4 antibodies by cells proximal to a tumor. The cells can be modified in vivo, or alternatively cells modified ex vivo can be administered to a patient by a variety of methods, such as by injection. By creating and/or introducing the transformed cells proximal to a tumor, the CTLA-4 blockade can be localized to the tumor.

In one embodiment, the cell is a tumor cell. For ex vivo transformation, such tumor cells can be irradiated to eliminate the ability of the cell to replicate, as known in the art, while maintaining the transient expression of anti-CTLA-4 antibodies after administration. For in vivo transformation, non-integrative expression vectors may be preferred.

In certain preferred embodiments, the tumor cell is autologous or endogenous. In the former instance, the tumor cell is taken from a patient, transfected or transduced with a construct encoding an anti-CTLA-4 antibody, and re-introduced to the patient, for example after irradiation. In the latter instance, the tumor cell is transformed in vivo by local administration of an appropriate construct as described herein.

In an alternative embodiment, the modified tumor cell is allogeneic. The allogeneic tumor cell thus can be maintained in a cell line. In this instance, the tumor cell can be selected from the cell line, irradiated, and introduced to the patent.

In another alternative embodiment, the modified human cells are antigen-presenting cells such as dendritic cells, or monocytes.

Without being bound to a particular theory or mode of action, dendritic cells can serve as hubs where T-cells become primed to attack tumor cells bearing a given antigen. Dendritic cells are laden with surface B7 molecules, which could switch off potentially responsive T-cells that express CTLA-4 prematurely (e.g. while still in the vicinity of the APC, usually within a lymph node). Preferably, APCs expressing anti-CTLA-4 Abs can increase the intensity and duration of the anti-tumor T-cell response primed by the APC.

In another alternative embodiment, the modified human cells are T cells. In one embodiment, T cells specific for particular tumor antigens can be transformed and expanded ex vivo and re-infused into patients. Again, without being bound by a particular theory or mode of action, by expressing anti-CTLA-4 Abs the T cells may protect themselves and other endogenous and/or adoptively transferred tumor-specific T-cells from being silenced by lack of costimulation or suppressive APCs in the tumor environment.

Modified human cells capable of producing the anti-CTLA-4 antibodies can be made by transfecting or transducing the cells with an expression vector encoding an anti-CTLA-4 antibody. The anti-CTLA-4 expression vector can be made by methods well known in the art.

In certain preferred embodiments, the anti-CTLA-4 antibody is an scFv molecule. scFv molecules may be produced for example, as described by Smith et al. Gene Ther. 2003 August; 10(15):1248-57. Likewise, scFv antibodies may be produced as described by Wang et al., J Immunol Methods, 2000 233(1-2):167-77, which is incorporated herein by reference in its entirety.

In various embodiments, the anti-CTLA-4 antibody can be administered to a patient in the form of a nucleic acid construct.

In one embodiment, the construct comprises a retroviral vector. Retroviral vectors are capable of permanently integrating DNA encoding the anti-CTLA-4 antibody into the cell genome. Thus, in the case of ex vivo manipulation of autologous or allogeneic cells, stable cell lines that constitutively produce the anti-CTLA-4 antibody can be prepared. In a preferred embodiment, the cells are irradiated prior to administration to a patient. The irradiated cells produce the anti-CTLA-4 antibody for a limited period of time In one embodiment, the anti-CTLA-4 antibody construct comprises an SFV vector, which demonstrates high levels of transient expression in mammalian cells. The SFV vector is described, for example, in Lundstrom, *Expert Opin. Biol. Ther.* 3:771-777 (2003), incorporated herein by reference in its entirety. Thus, in the case of in vivo manipulation of endogenous cells in a patient, transient expression of high levels of the anti-CTLA-4 antibody can be accomplished. This is to prevent constitutive expression, and permanent blockade, of the CTLA-4 signaling pathway in vivo.

Systems capable of expressing antibodies in vivo are known in the art. By way of example and not limitation, the system can use the 2A mediated antibody expression system disclosed in Fang et al., Nature Biotech. 23(5) 2005 and U.S. Patent Publication 2005/0003508, the disclosures of which are expressly incorporated by reference herein in their entirety. Other systems known in the art are contemplated, and can also be adapted to produce anti-CTLA-4 antibodies in vivo as described herein.

Administration of the anti-CTLA-4 producing cells disclosed herein can be combined with administration of cytokines that stimulate antigen-presenting cells such as granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), etc., or cellular vaccines capable of expressing such cytokinesin preferred embodiments, the anti-CTLA-4 producing cells are further modified to express such cytokines. Additional proteins and/or cytokines known to enhance T cell proliferation and secretion, such as IL-1, IL-2, B7, anti-CD3 and anti-CD28 can be employed simultaneously or sequentially with the blocking agents to augment the immune response. The present therapy can also be combined with any of the molecules, or conducted as described in, U.S. Pat. No. 6,051,227, incorporated herein by reference in its entirety.

Anti-CTLA-4 Vectors and Methods of Transformation

Anti-CTLA-4 expression vectors of the invention may be viral or non-viral. Viral vectors are preferred for use in vivo. Anti-CTLA-4 expression vectors of the invention comprise an anti-CTLA-4 antibody encoding nucleic acid, or a complement thereof, operably linked to an expression control region, or complement thereof, that is functional in a mammalian cell. The expression control region is capable of driving expression of the operably linked anti-CTLA-4 antibody encoding nucleic acid such that anti-CTLA-4 antibody is produced in a human cell transformed with the anti-CTLA-4 expression vector.

Expression control regions are regulatory polynucleotides (sometimes referred to herein as elements), such as promoters and enhancers, that influence expression of an operably linked nucleic acid.

An expression control region of an anti-CTLA-4 expression vector of the invention is capable of expressing operably linked anti-CTLA-4 antibody encoding nucleic acid in a human cell. In one embodiment, the cell is a tumor cell. In one embodiment, the cell is a non-tumor cell.

In one embodiment, the expression control region confer regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

Especially preferred for use in the present invention are inducible promoters capable of effecting high level of expression transiently in response to a cue. When in the proximity of a tumor cell, a cell transformed with an anti-CTLA-4 expression vector comprising such an expression control, sequence is induced to transiently produce a high level of anti-CTLA-4 antibody by exposing the transformed cell to an appropriate cue.

Preferred inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of an anti-CTLA-4 coding sequence into mRNA. A promoter will have a transcription initiating region, which is usually placed proximal to the 5' end of the coding sequence, and typically a TATA box, using a located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also preferred for in vivo transduction (e.g., Dzau et al., Trends in Biotechnology 11, 205-210 [1993]). In some situations it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene therapy protocols see Anderson et al., Science 256, 808-813 (1992).

Where appropriate, gene delivery agents such as, e.g. integration sequences can also be employed. Numerous integration sequences are known in the art (see for example Nunes-Duby et al., Nucleic Acids Res. 26:391-406, 1998; Sadwoski, J. Bacteriol., 165:341-357, 1986; Bestor, Cell, 122(3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al, Cell, 29:227-234, 1982) R (Matsuzaki, et al, J. Bacteriology, 172:610-618, 1990), φC31 (see for example Groth et al., J. Mol. Biol. 335:667-678, 2004), sleeping beauty, transposases of the mariner family (Plasterk et al., supra), and components for integrating viruses such as AAV, retroviruses, and lentiviruses having components that provide for virus integration such as the LTR sequences of retroviruses or lentivirus and the ITR sequences of AAV (Kootstra et al., Ann. Rev. Pharm. Toxicol., 43:413-439, 2003).

Anti-CTLA-4 Viral Vectors

In one aspect, the invention provides anti-CTLA-4 expression vectors that are anti-CTLA-4 Ab viral vectors. Many viral vectors useful for gene therapy are known (see, for example, Lundstrom, Trends Biotechnol., 21:117, 122, 2003.

Preferred viral vectors include those selected from the group consisting of lentiviruses (LV), retroviruses (RV), adenoviruses (AV), adeno-associated viruses (AAV), and alpha viruses, though other viral vectors may also be used. For in vivo uses, viral vectors that do not integrate into the host genome are preferred, such as alpha viruses and adenoviruses, with alpha viruses being especially preferred. Preferred types of alpha viruses include Sindbis virus, Venezuelan equine encephalitis (VEE) virus, and Semliki Forest virus (SFV), with SFV being especially preferred. See, for example, Lundstrom, Expert Opin. Biol. Ther. 3:771-777, 2003; Afanasieva at al. Gene Ther., 10:1850-59, 2003. For in vitro uses, viral vectors that integrate into the host genome are preferred, such as retroviruses, AAV, and lentiviruses.

In a preferred embodiment, the viral vector provides for transient high level expression in a transduced human cell.

In one embodiment, the viral vector does not provide for integration of a CTLA-4 Ab encoding nucleic acid into the genome of a transduced human cell.

In another embodiment, the viral vector provides for integration of a CTLA-4 Ab encoding nucleic acid into the genome of a transduced human cell.

In one embodiment, the invention provides methods of transducing a human cell in vivo, comprising contacting a solid tumor in vivo with an anti-CTLA-4 Ab viral vector of the invention.

In another embodiment, the invention provides methods of transducing a human cell ex vivo, comprising contacting a human cell ex vivo with an anti-CTLA-4 Ab viral vector of the invention. In one embodiment, the human cell is a tumor cell. In one embodiment, the human cell is allogeneic. In one embodiment, the tumor cell is derived from the patient. In one embodiment, the human cell is a non-tumor cell, such as, e.g., an antigen presenting cell (APC), or a T cell.

Virus particle coats may be modified to alter specificity and improve cell/tissue targeting, as is well known in the art. Viral vectors may also be delivered in other vehicles, for example, liposomes. Liposomes may also have targeting moieties attached to their surface to improve cell/tissue targeting.

The present application is directed to human cells expressing an anti-CTLA-4 antibody that specifically binds to the extracellular domain of CTLA-4 and inhibits CTLA-4-mediated negative signaling. In certain embodiments, the human cell expresses the anti-CTLA-4 antibody proximal to a tumor cell for example in a cancer patient. Thus, the human cell is capable of localized expression of the antibody at a tumor cell or tumor cell mass. The anti-CTLA-4 antibody can inhibit CTLA-4 signaling in cells proximal to said tumor cell, and/or break immune tolerance against a tumor-associated self antigen and stimulate an autoreactive T cell response to said tumor cell. In a preferred embodiment, localized expression of the anti-CTLA-4 antibody reduces or inhibits undesired adverse immune responses.

It is not necessary for the practice of the invention that the mechanism of action be understood. The cells and methods described herein provide human cells proximal to tumor cells or tumor cell masses. Expression of anti-CTLA-4 antibodies and optionally additional cytokines in proximity to the tumor cells releases responding T cells from inhibitory signals mediated through CTLA-4.

CTLA-4 Antibodies

Anti-CTLA-4 antibodies are molecules that specifically bind to the extracellular domain of CTLA-4 protein, and block the binding of CTLA-4 to its counter-receptors, CD80 and CD86. In preferred embodiments, the binding affinity of the antibody will be at least about 100 uM. The antibodies are substantially unreactive with related molecules to CTLA-4, such as CD28 and other members of the immunoglobulin superfamily. Blocking antibodies that do not activate CTLA-4 signaling are preferred. Conveniently, this is achieved by the use of monovalent or bivalent binding molecules. Suitable anti-CTLA-4 antibodies may also include those disclosed in U.S. Pat. Nos. 5,855,887, 5,811,097, 6,051,227, 6,984,720, 6,682,736, 6,979,442, 7,109,003, and 7,132,281, each of which is incorporated by reference herein in its entirety.

As used herein, the term "antibody" refers to a monomeric or multimeric protein comprising one or more polypeptide chains. An antibody binds specifically to an antigen (e.g. the extracellular portion of CTLA-4) and may be able to inhibit or modulate the biological activity of the antigen. As used herein, the term "antibody" also includes antibody fragments. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird at al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sol. U.S.A. 90:6444-6448). In certain embodiments, antibodies are produced by recombinant DNA techniques. In additional embodiments, antibodies are produced by enzymatic or chemical cleavage of naturally occurring antibodies.

In certain embodiments, an anti-CTLA-4 antibody can be designed to have any isotype, for example, IgG (including IgG1, IgG2, IgG3, IgG4). In some embodiments, the hinge region of an anti-CTLA-4 antibody of the invention is of an immunoglobulin selected from the group consisting of IgG1, IgG2, IgG3, IgG4.

In preferred embodiments, the anti-CTLA-4 antibodies are designed or engineered to reduce or eliminate effector function. Antibodies elicit four main effector functions: ADCC, phagocytosis, complement-dependent cytotoxicity (CDC), and half life/clearance rate. ADCC and phagocytosis are mediated through interaction of cell-bound monoclonal antibodies with Fc gamma receptors (FcγR), CDC by interaction of cell-bound mAbs with the series of soluble blood proteins that constitute the complement system (e.g., C1q), and for half-life by binding of free monoclonal antibody to the neonatal Fc receptor (FcRn). Presta, Current Pharmaceutical Biotechnology (2002), 237-256. Proper glycosylation of the Fc region of a monoclonal antibody (such as IgG) is thought to be important in conferring wild type effector functions. See, for e.g., Jefferis & Lund, Immunol. Lett. (2002), 82(1-2): 57-65; Lisowska, Cell. Mol. Life Sci. (2002), 59(3): 445-455; Radaev & Sun, Mol. Immunol. (2002), 38(14): 1073-1083; Mimura et al., Adv. Exp. Med. Biol. (2001), 495: 49-53; Rudd at al., Science (2001), 291(5512): 2370-2376; Jefferis et al., Immunol. Rev. (1998), 163: 59-76; Wright & Morrison, Trends Biotechnol. (1997), 15(1): 26-32; Jefferis & Lund, Chem. Immunol. (1997), 65: 111-128.

In one aspect, specific effector functions (e.g. FcγR binding that regulates antibody-dependent cell-mediated cytotoxicity (ADCC) and/or phagocytosis) can be ablated or reduced by modifying specific amino acids that correlate with the effector functions. Exemplary modifications have been disclosed in, for example, Hsu et al., Transplantation (1999), 27: 68(4): 545-554; Carpenter et al., J. Immunol. (2000), 165: 6205-6213; Xu et al., Cell. Immunol. (2000), 200: 16-26; Van der Lubbe et al., Arthritis Rheum: (1993), 36(10): 1375-1379; Kon et al., Lancet (1998), 352: 1109-1113; Reddy et al., J. Immunol. (2000), 164: 1925-1933; Duncan et al., Nature (1988), 332: 563-564; Klein et al., Proc. Natl. Acad. Sci. USA (1981), 78(1): 524-528; Gillies & Wesolowski, Hum. Antibod. Hybridomas (1990), 1(1): 47-54; and Armour et al., Eur. J. Immunol. (1999), 29: 2613-2624, each of which is incorporated by reference herein in its entirety. Of course, the antibody modifications can be designed in such a way to ensure that they do not significantly compromise the pharmacokinetic characteristics of the modified antibody. For example, retention of substantially wild type in vivo half life or clearance is important in many clinical settings. In a preferred embodiment, the anti-CTLA-4 antibodies are selected or modified to reduce or eliminate one or more effector functions.

In another aspect, antibody fragments in particular can exhibit a number of benefits over intact IgG. For example, antibody fragments have a shorter half-life than intact IgG, because they are more rapidly removed from the circulation by the kidneys as a result of their lower molecular weight, thus reducing potential toxicity (Behr et al., 1995). Another advantage of the reduced size is that they may penetrate tumor tissue and associated vasculature more readily ((Yokota et al., 1992). In this way, more cells of the tumor mass are targeted.

In a further aspect, anti-CTLA-4 antibodies that lack an Fc region provide advantages over antibodies that have an Fc region or a portion thereof. Such fragments do not induce activation of immune responses, as the ability to bind complement and Induce a complement cascade is absent. In other embodiments, divalent anti-CTLA-4 antibody fragments (e.g. F(ab')$_2$ fragments) that bind CLTA-4 with higher avidity than monovalent anti-CTLA-4 antibody fragments (e.g. F(ab') fragments) are preferred.

In preferred embodiments, the anti-CTLA-4 antibodies demonstrate reduced affinity for Fc receptors. Reduced affinity for Fc receptors can be engineered in a variety of ways, for example, by selecting an antibody fragment lacking a specific Fc receptor binding region, as above, or by mutating the Fc portion of the antibody at one or more positions that reduce Fc receptor binding. See, e.g., U.S. Patent Pubs. 2005/0152894, 2004/0132101, and 2005/0054832, the disclosures of which are each expressly incorporated by reference herein in their entireties. The antibodies can be designed to avoid a complement cascade, and reduce immune reactivity against T cells.

In one embodiment, the anti-CTLA-4 antibodies are designed to have reduced or eliminated intermolecular disulfide linkage (e.g., disulfide linkage between two heavy chains). In some embodiments, said inter-heavy chain disulfide linkage is between Fc regions. In another embodiment, an antibody of the invention comprises a variant heavy chain hinge region incapable of, or that participate in, intermolecular disulfide linkage. In one embodiment, said variant hinge region lacks at least one cysteine, at least two, at least three, at least four, or any integer number up to all, cysteines normally present in a wild type hinge region that are capable of forming an intermolecular (e.g., inter-heavy chain) disulfide linkage. In general, antibodies of the invention possess substantially similar biological (such as, but not limited to, antigen binding capability) and/or physicochemical characteristics relevant for therapeutic effects as their wild type counterparts, except that antibodies of the invention substantially lack at least one, but not all, of the effector functions of the wild type counterpart antibody. Such embodiments are described in more detail in U.S. Patent No. 2005/0152894, incorporated herein by reference in its entirety.

In some embodiments, the invention provides an antibody comprising a variant hinge region of an immunoglobulin heavy chain, wherein said variant hinge region lacks (i.e., does not comprise or contain, or is free of) a cysteine residue capable of forming a disulfide linkage. In some embodiments, said disulfide linkage is intermolecular (preferably inter-heavy chain). In some embodiments of antibodies wherein two or more cysteines are rendered incapable of disulfide linkage, all said cysteines are normally capable of intermolecular (preferably inter-heavy chain) disulfide linkage. In some embodiments of antibodies wherein two or more cysteines are rendered incapable of disulfide linkage, at least one of said cysteines is normally capable of intermolecular (for example, inter-heavy chain) disulfide linkage. In some embodiments, said intermolecular disulfide linkage is between cysteines of two immunoglobulin heavy chains.

In a preferred embodiment, the antibody is an scFv molecule. The scFv molecule, for example, can have the sequence disclosed herein. scFv molecules can be produced by any methods known in the art. Anti-CTLA-4 scFv molecules have been described, for example, by Chen at al., Protein Expr. Purif. 2005, electronic publication. In a preferred embodiment, the scFv antibody fragments are produced as described in Gilliland at al., Tissue Antigens 1996, 47:1-20, which is incorporated herein by reference in its entirety. The anti-CTLA-4 antibodies disclosed herein are secreted.

In various embodiments, different C-terminal tail appended to the anti-CTLA-4 antibody to facilitate different outcomes of binding to CLTA-4. Applicants note that an antibody (e.g. full length antibody or antibody fragment) can Include an IgG tail (e.g. IgG1, IgG2, IgG3, or IgG4). In one embodiment, an anti-CTLA-4 antibody can be designed to prevent dimerization of IgGs and reduce Fc receptor binding. For example, an anti-CTLA4 antibody can include an IgG1 constant region in which the hinge cysteine residues have been changed to serine residues to prevent dimerization and to reduce Fc-receptor binding. This antibody variant binds CTLA-4 and may block its interaction with B7 (the constant region helps stabilize binding and provides additional bulk for blockade). Low Fc-receptor binding reduces the chance of the scFv being bound on the surface of APCs where it could cross-link CTLA-4 on the surface of T-cells and send a negative signal. In other exemplary embodiments, an scFv can be modified to include an IgG1 tails with the hinge cysteines mutated to serines or simple tags as tails. The Ig tail mutations can prevent dimerization, thereby reducing Fc receptor binding and any capacity for ADCC type effects.

In still other embodiments, the tail of the anti-CTLA-4 antibody can exert a primarily immunosuppressive effect. Without being limited to a specific mechanism or action, such an effect can mimic anti-CTLA-4 antibodies tailed with a transmembrane region that anchors and keeps the antibody tethered to the cell surface. Such a CTLA-4 antibody can gain the ability to cross-link CTLA4 molecules on the surface of T-cells and send a tolerizing signal.

Methods of Administering Cells and Compositions

The human cells and viral vectors disclosed herein can be combined with a pharmaceutically acceptable carrier to form a pharmaceutical composition. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active cells or compositions, use thereof in the therapeutic compositions is contemplated. Supplementary compounds can also be incorporated into the compositions. Other pharmaceutically acceptable vehicles include conventional pharmaceutical effluents or additives.

Under ordinary conditions of storage and use, these preparations may contain a preservative to prevent the growth of microorganisms otherwise harmful to the patient.

Systemic Administration

In one embodiment, the human cells, viral vectors or compositions thereof can be provided systemically (i.e. the vectors or cells can be provided to the patient by circulation). When cells or viral vectors are provided systemically, the anti-CTLA-4 antibody is provided to all tissues. The cells or viral vectors administered systemically are not constrained to a specific location in the patient, but rather express the antibody and any other expression products throughout the patient. While not being limited to a single theory or mode of action, administration allows can allow transient or constitutive expression of the anti-CTLA-4 antibody and other expression products during the lifetime of the administered cells. Systemic distribution of the cells or viral vectors can thus act as a time-release delivery of the antibody and other expression products (e.g. co-expressed immune effector molecules). The administered cells eventually die and no longer produced the anti-CTLA-4 antibody, resulting in the decreased concentration and eventual elimination of anti-CTLA-4 antibodies (in the absence of further cell administration).

In one preferred embodiment, the cells or viral vectors can be administered together with a tumor cell vaccine. Both the tumor cell vaccine and the cells or viral vectors are co-administered. In a further variation, the cells themselves are autologous irradiated tumor cells.

The human cells, viral vectors and compositions can be administered in several different ways. Generally, the human cells, viral vectors and compositions can be administered in a convenient manner such as by injection (subcutaneous, intravenous, intramuscular, etc.), oral administration, inhalation, transdermal application, or rectal administration. The cells, viral vectors and compositions can also be administered parenterally or intraperitoneally. Depending on the route of administration, the cells, viral vectors and compositions may be coated in a material to protect the them from acids and other natural conditions which may kill or otherwise inactivate the cells or viral vectors.

In certain embodiments, compositions of cells or viral vectors are formulated to be suitable for injectable use. Such compositions can include sterile aqueous solutions (where water soluble) or dispersions and sterile powders for the extemporaneous preparation of sterile injectable solutions or dispersion. Preferably, the composition is sterile and fluid to the extent that easy syringability exists. The composition will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating one or more cells, viral vectors or compositions thereof, together or separately with additional immune response stimulating agents or immunosupressants, in the required amount in an appropriate solvent with one or a combination of ingredients enumerated above, as required, followed by filtered sterilization. Generally, dispersions are prepared by incorporating the cells or compositions into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the treated patients; each unit containing a predetermined quantity of cells or viral vectors calculated to produce the desired therapeutic effect in association with the required pharmaceutical carrier. The specification for the dosage unit forms of the invention are dictated by and directly dependent on (a) the unique characteristics of the cells, viral vectors or compositions and the particular therapeutic effect to be achieved, and (b) the limitations inherent in the art of compounding such an agent for the treatment of sensitivity in individuals.

The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the cells, viral vectors or composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The toxicity and therapeutic efficacy of the human cells, viral vectors and compositions described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While cells, viral vectors and compositions that exhibit toxic side effects may be used, care should be taken to design a delivery system that targets such cells, viral vectors and compositions to the site of affected tissue in order to minimize potential damage to uninfected cells and, thereby, reduce side effects.

In one embodiment, a therapeutically effective amount of the cell, viral vector or composition is administered to a patient. The optimal dose of the cell or viral vector given may even vary in the same patient depending upon the time at which it is administered.

The skilled artisan will appreciate that certain factors may influence the dosage required to effectively treat a patient, including but not limited to the severity of the disease or disorder, previous treatments, the general health and/or age of the patient, and other diseases present. Moreover, treatment of a patient with a therapeutically effective amount of the cell, viral vector or composition can include a single treatment or, preferably, can include a series of treatments. It will also be appreciated that the effective dosage of cells, viral vectors or compositions produced by the cell or viral vector used for treatment may increase or decrease over the course of a particular treatment. Changes in dosage may result from the results of assays designed to monitor tumor status as is well known in the art.

Actual methods for preparing parenterally administrable cells, viral vectors and compositions are known or apparent to those skilled in the art and are described in more detail in, for example, Remington's Pharmaceutical Science, 15th ed., Mack Publishing Company, Easton, Pa. (1980), which is incorporated herein by reference.

The cells, viral vectors and compositions can be administered for prophylactic and/or therapeutic treatments. In therapeutic application, compositions can be administered to a patient already suffering from a disease, in an amount sufficient to reduce or at least temporarily limit tumor growth and related complications. An amount adequate to accomplish this is defined as a "therapeutically effective dose."

Amounts effective for this use will depend upon the clinical situation and the general state of the patient's own immune system. For example, doses for preventing transplant rejection may be lower than those given if the patient presents with clinical symptoms of rejection. Single or multiple administrations of the compositions can be carried out with dose levels and pattern being selected by the treating physician. In any event, the pharmaceutical formulations should provide a quantity of the cells, viral vectors or compositions described herein sufficient to effectively treat the patient.

The pharmaceutical compositions can be included in a container, pack, or dispenser together with instructions for administration. Kits for practice of the instant invention are also provided. For example, such a kit comprises a human cell, viral vector or composition comprising a cell and/or viral vector, together with a means for administering the cell, viral vector or composition, e.g., one or more syringes. The kit can come packaged with instructions for use.

Administration at the Site of Tumor

In preferred embodiments, the anti-CTLA-4 producing cells or anti-CTLA-4 encoding vectors can be provided at, e.g. within or contacting the tumor tissue, or proximal to the location of a tumor. By "proximal to" is meant within an effective distance of the tumor cell, such that the anti-CTLA-4 antibodies resulting from the expression vectors and/or transformed cells of the invention will reach the tumor tissue directly. The subject methods of providing or creating the modified cells or viral vectors at the tumor site thus provide the anti-CTLA-4 antibodies expressed by the modified cells or viral vectors locally to the tumor, while minimizing exposure of anti-CTLA-4 antibodies to surrounding non-tumor cells. Without being limited to a specific mode of activity, direct administration of the cells, viral vectors or composition to the tumor provides a direct and sustained benefit to the tumor, while reducing autoimmune and immunosuppressive side effects that can be observed in systemic administration.

Methods of administering cells or viral vectors directly to tumors have been accomplished in other contexts. For example, cells have been administered to a tumor site by injection Rodriguez-Madoz et al., *Molecular Therapy* (2005) 12, 153-163, incorporated by reference herein in its entirety.

The human cells or viral vectors can be selected to bind directly to tumor cells. For example, human T lymphocytes can be modified to express the anti-CTLA-4 antibodies, and optionally other co-expressed molecules. T lymphocytes may be modified by methods known in the art. In some cases, the T lymphocytes can be modified as disclosed in Sadelaine et al., Nature Reviews Cancer 3, 35-45 (2003). T lymphocytes have also been used for site specific administration to treat autoimmunity disease, as disclosed by Tamer et al., Methods of Autoimmunity Reviews 5(2):143-152, February 2006.

Human cells can be selected to bind directly to tumor cells either alternatively, or in addition to, direct administration of cells and compositions to a tumor site.

Administration at the Lymph Node Nearest a Tumor

In still other embodiments, cells can be administered directly, or proximal to, the lymph nodes near the tumor. The cells and compositions can be administered to the lymph nodes by any means disclosed herein.

EXPERIMENTAL

The following description of examples is purely exemplary, and merely illustrate aspects of the present invention.

Example 1

The 9D9 mouse anti-mouse CTLA4 antibody was typed using the IsoStrip kit from Roche diagnostics. The 9D9 antibody was determined to be IgG2b-κ (data not shown).

Example 2

The 9D9 antibody was cloned into Ig: FIG. 1 shows the cloning strategy.

Redundant primers for the 9D9 light chain and heavy chain were designed based on Wang, Z and Ratner, D (*J Immunol Methods*, 2000 Jan. 13; 233(1-2):167-77) to amplify the light chain ($V_L$) and heavy chain ($V_H$) variable regions. PCR was performed using the Advantage 2 PCR kit from Clontech to generate products with T-A ends, and using a 3:1 mix of Vent (NEB) and Pfu (Stratagene) polymerases to generate blunt-ended fragments. FIG. 2 shows the sequences of the light and heavy chain primers.

A low, 45 degree annealing temperature was used to promote hybridization of partially mis-matched primer/template sequences. Primers were designed to contain restriction sites to facilitate subsequent cloning of the $V_H$ and $V_L$ PCR producers as well as to append a $(Gly_4Ser)_3$ linker at the tail of the VL and head of the VH for later joining.

Blunt ended PCR products were cloned using the Zero Blunt PCR Cloning Kit (Invitrogen), while PCR products with T-A overhangs were cloned using the Topo TA Kit (Invitrogen).

Figure 3:
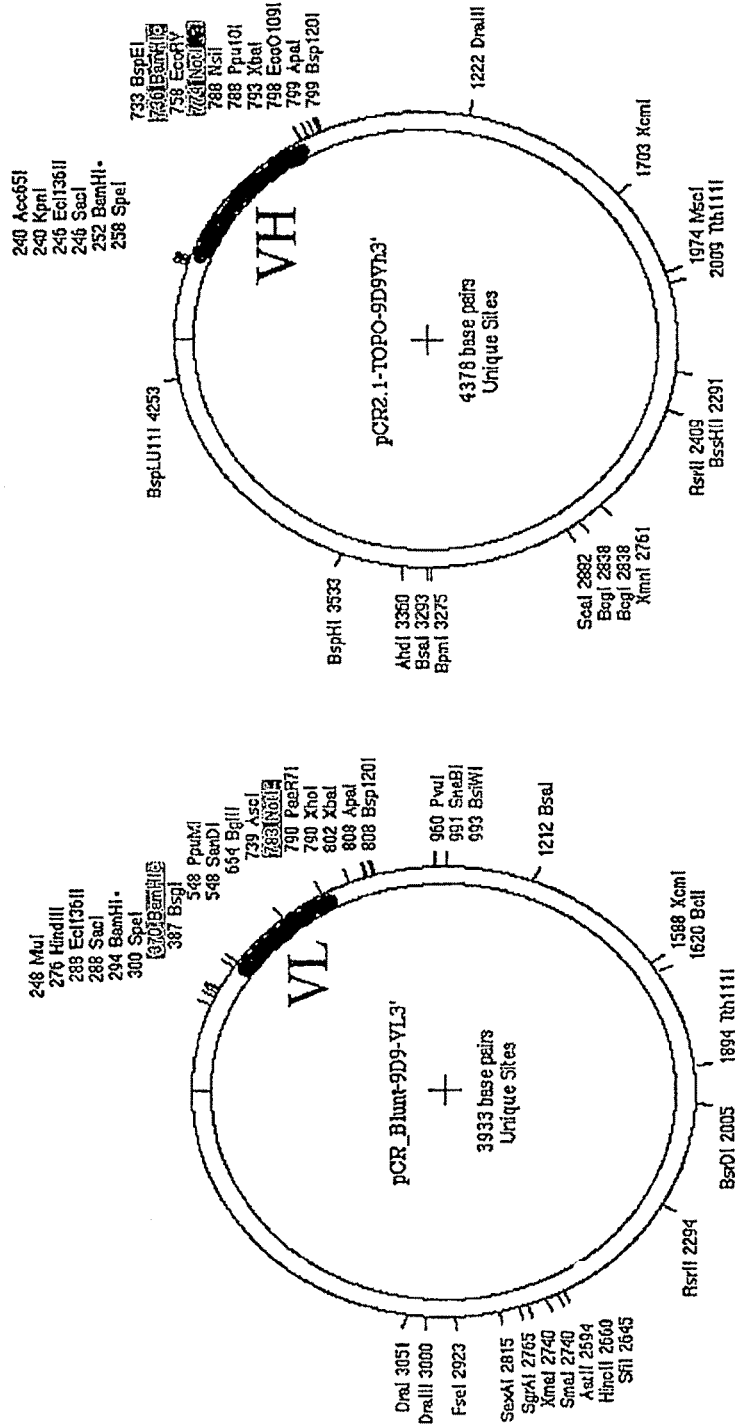
FIG. 3 depicts VL and VH constructs used to produce the 9D9 antibody.

Following transformation into Top10 competent cells, colonies were selected and expanded. DNA was isolated using the Qiagen Spin Mini-prep kit and screened by digestion with EcoRI (NEB). The final VL and VH constructs are depicted in FIG. 3.

The 9D9 antibody by SOE PCR. Individual VH and VL fragments were amplified by PCR as described above and then gel purified using the Qiagen Gel Extraction Kit. The purified fragments were then used as templates in a PCR reaction using the upstream 5' Mk-FR1 primer and the 3' IgG2B primer and the 3:1 Vent (NEB) to Pfu1 (Stratagene) mixture as previously. The overhanging region containing the Gly-Ser linker allows the amplified VH and VL fragments to hybridize and serve as a single template for amplification which contains the 2 fragments joined by the central Gly-Ser linker. Following amplification the DNA was run on a 1% agarose gel and the 821 bp fragment representing the full scFv was isolated and purified using the Qiagen Gel Extraction kit. This fragment was then cloned using the Zero Blunt PCR cloning kit (Invitrogen).

Figure 4:
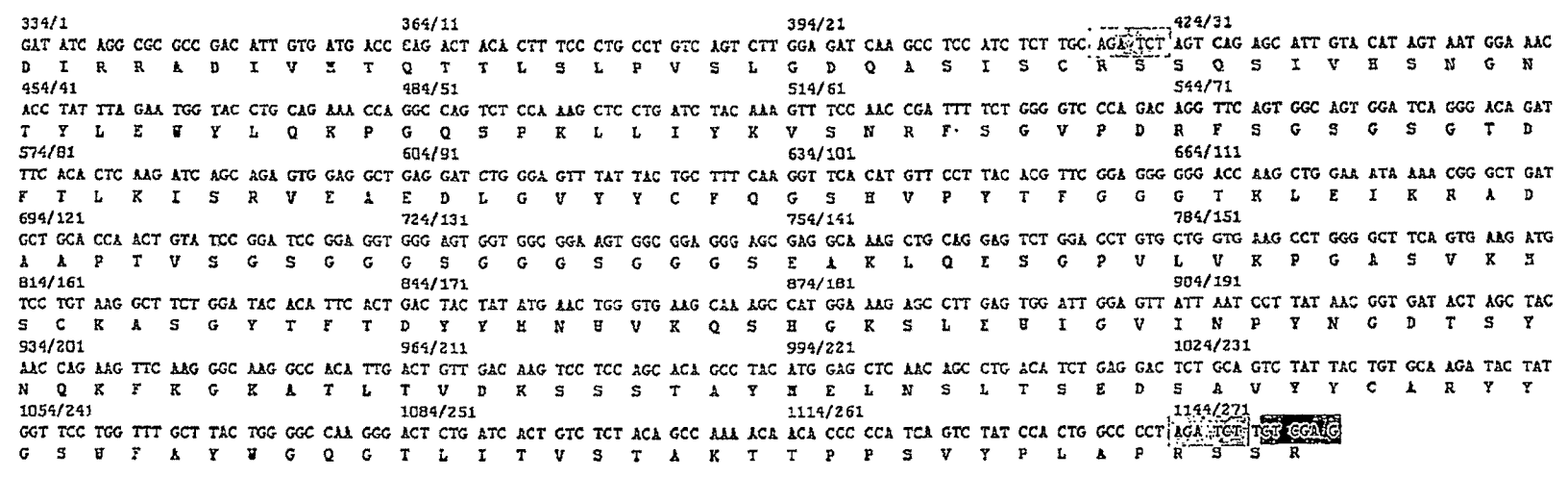

FIG. 4 shows the sequence of the 9D9 scFv molecule.

The complete 9D9 scFv was cloned into the pSecTag2-HygroA vector (Invitrogen) which provides a 5' Ig-kappa secretion signal and a 3' Myc-6×HIS tail. Also the scFv was cloned into a modified pSecTag2 which provides the 5' secretion signal and a 3' IgG1 tail with the hinge cysteines mutated to serines.

Example 3

Figure 5:
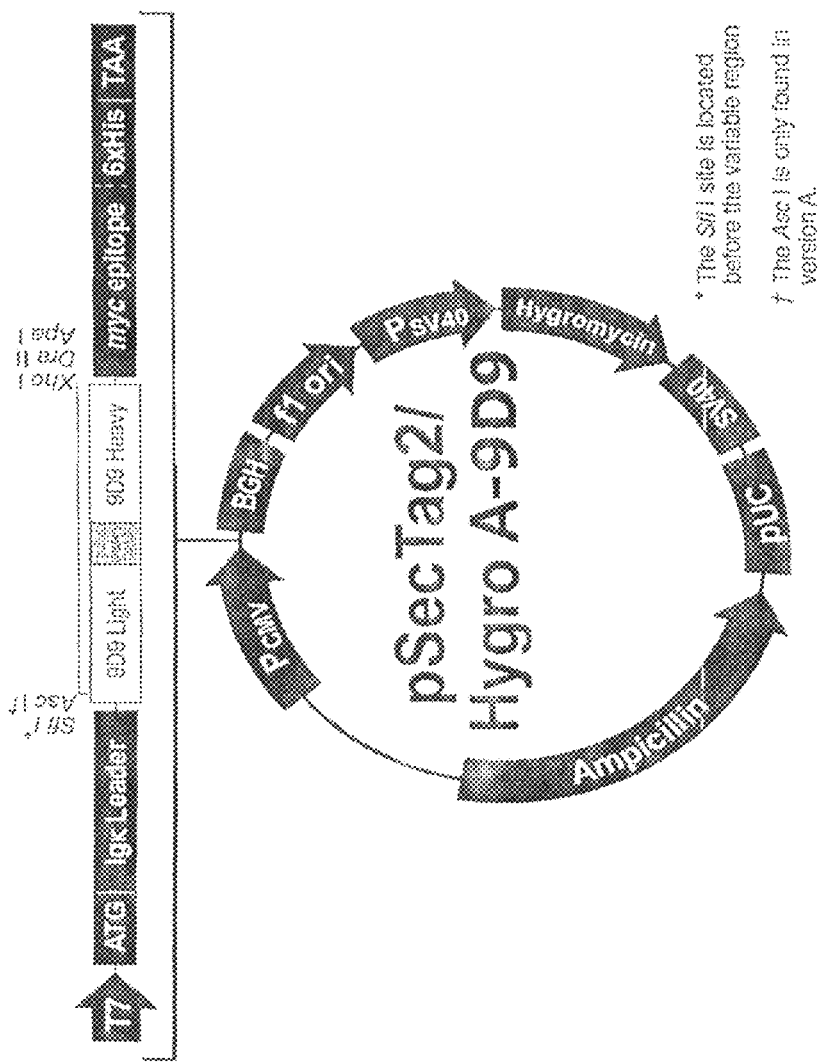
FIG. 5 depicts an expression vector used for production of the myc-HIS tailed 9D9 scFv molecule.
Figure 6:
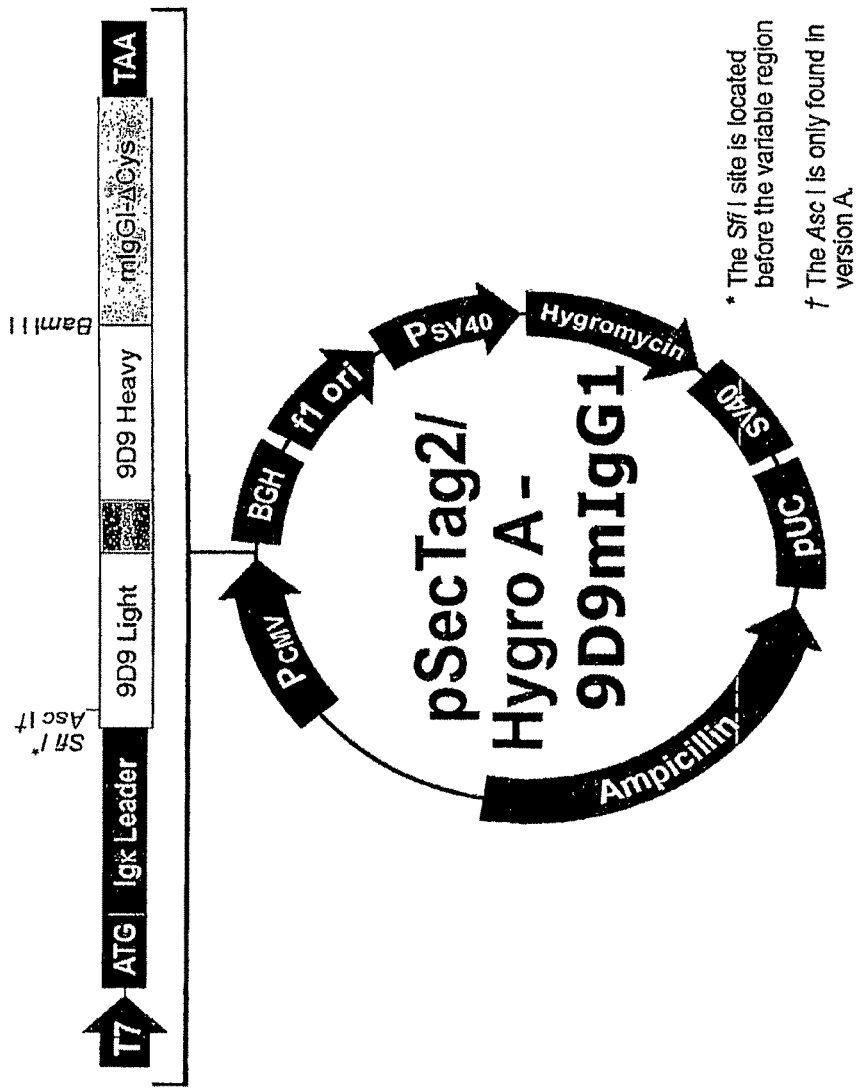
FIG. 6 depicts an expression vector used for production of the IgG1 tailed version of the 9D9 scFv molecule.
Figure 7:
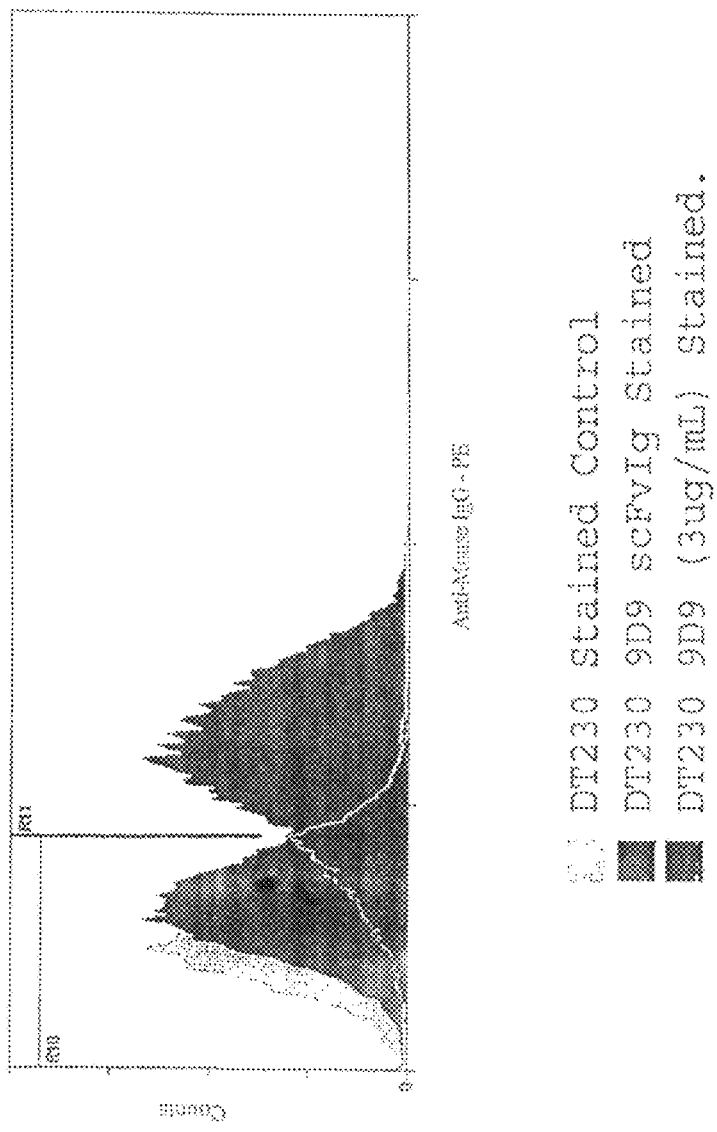
FIG. 7 depicts a CD spectrum of scFv antibodies against DT230 cells expressing surface CTLA-4 protein.
Figure 8:
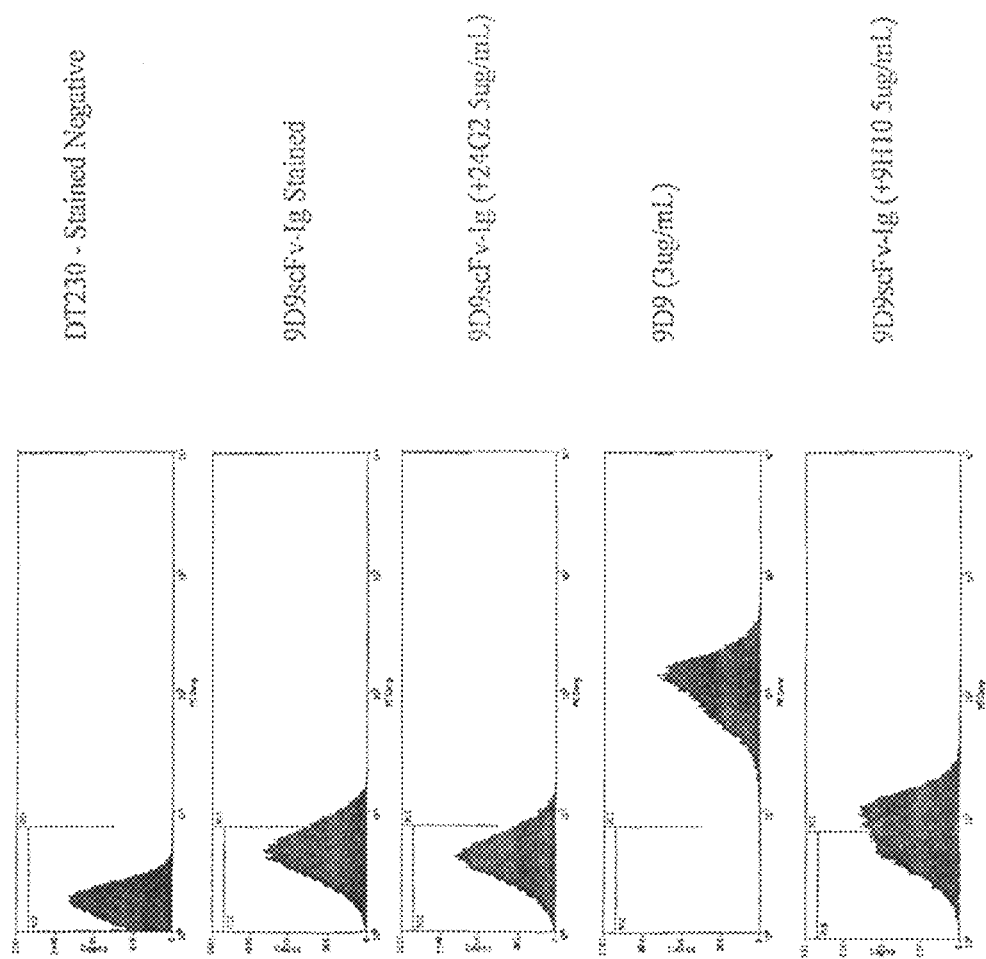
FIG. 8 depicts various CD spectra of scFv antibodies against DT230 cells expressing surface CTLA-4 protein.

MLV-based retroviral vectors expressing the Myc-HIS tailed and the IgG1 tailed versions of the 9D9 scFv were used to make 293T cells stably expressing each of the scFv molecules. FIG. 5 shows the expression vector used for production of the myc-HIS tailed 9D9 scFv molecule, and FIG. 6 shows the expression vector used for production of the IgG1 tailed version of the 9D9 scFv molecule.

Supernatants from these cells were collected and used to stain DT230 cells (a mouse L-cell line which expresses high levels of surface CTLA4). scFv bound to the surface of these cells was quantitated using an anti-mouse-PE secondary antibody and analyzed by flow cytometry on a Cyan-LX (Dako-Cytomation).

Figure 12:
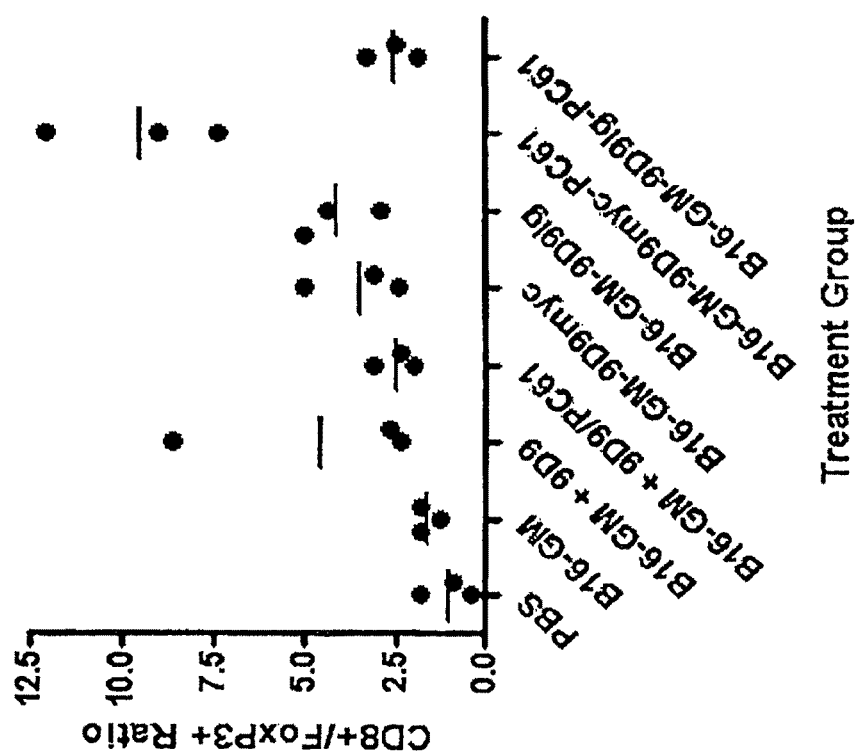
FIG. 12 depicts the intra-tumor T-cell profile in mice 18 days after treatment with the shown anti-CTLA-4 monoclonal antibodies and scFv molecules.
Figure 13:
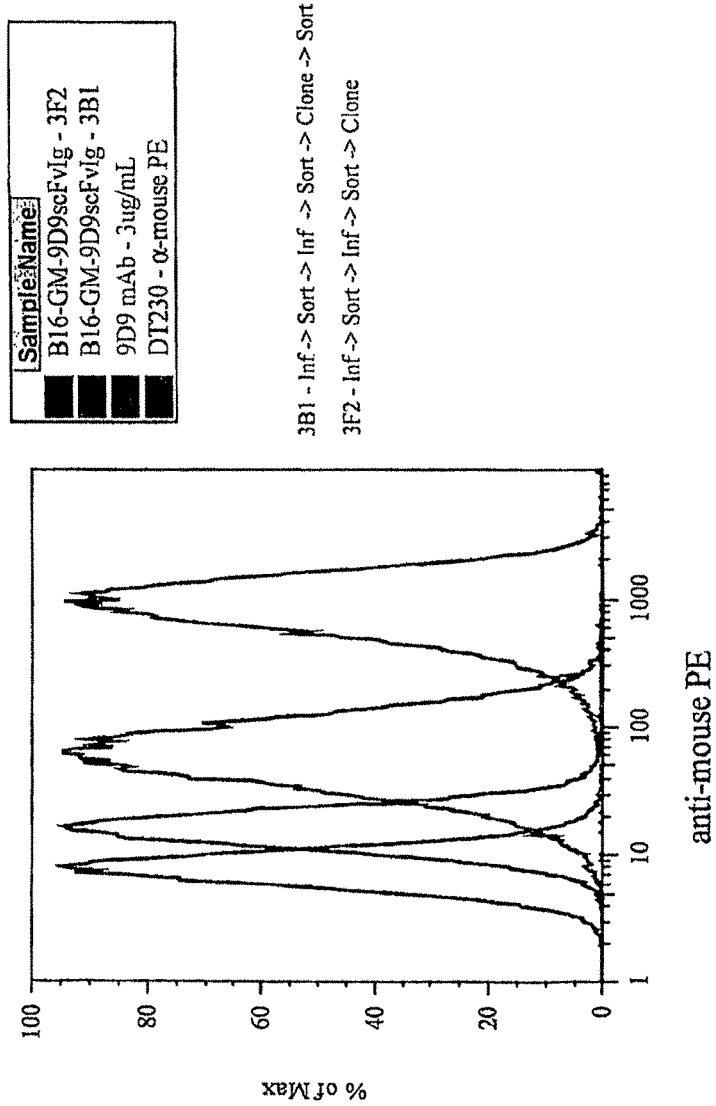
FIG. 13 depicts DT230 staining of B16-GM-9D9scFv Ig cell lines with DT230 raw supernatant and anti-mouse PE.

FIGS. 12 and 13 show CD specta of scFv antibodies against DT230 cells expressing surface CTLA-4 protein.

Example 4

GMVax-9D9scFv Cell Lines were created.

MLV-based retroviral vectors expressing each form of the 9D9 scFv and a truncated primate NGFp75 surface marker were used to transduce B16-GMCSF cells.

Positive cells were detected by staining with a mouse anti-primate NGF primary and anti-mouse APC secondary antibody (Pharmingen) and sorted by FACS on a MoFlo (Cytomation). Additionally, and anti-Lyt2-PE antibody (Pharmingen) was used to select for high levels of GMCSF expression.

Figure 9:
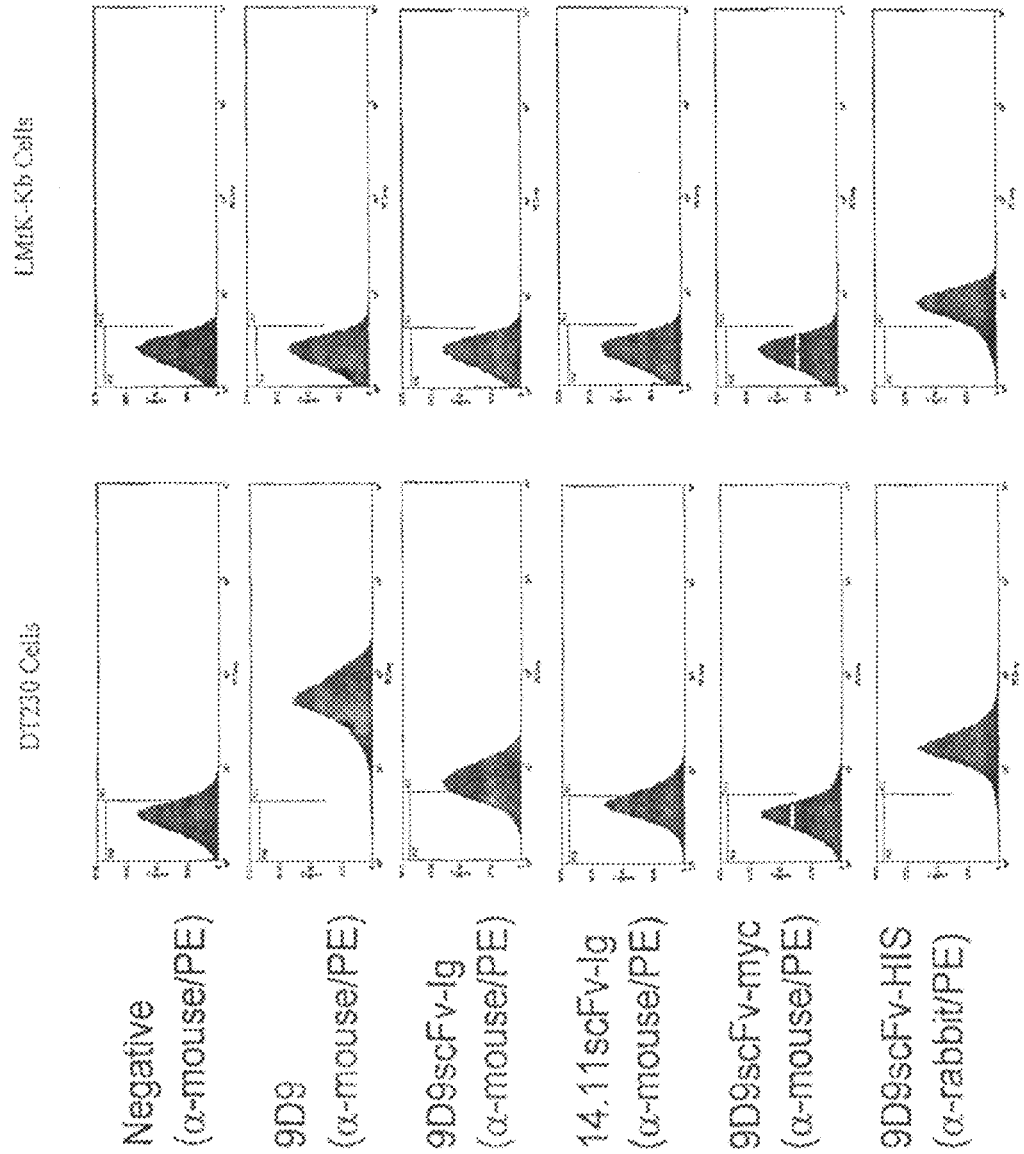
FIG. 9 depicts DT230/LMtK comparative histograms of the 9D9 antibody and various forms of the scFv molecules.

FIG. 9 shows DT230/LMtK comparative histograms of the 9D9 antibody and various forms of the scFv molecules.

Example 5

MLV-based retroviral vectors expressing each form of the 9D9 scFv and a truncated primate NGFp75 surface marker were used to transduce B16-GMCSF cells.

Positive cells were detected by staining with a mouse anti-primate NGF primary and anti-mouse APC secondary antibody (Pharmingen) and sorted by FACS on a MoFlo (Cytomation). Additionally, and anti-Lyt2-PE antibody (Pharmingen) was used to select for high levels of GMCSF expression.

Figure 10:
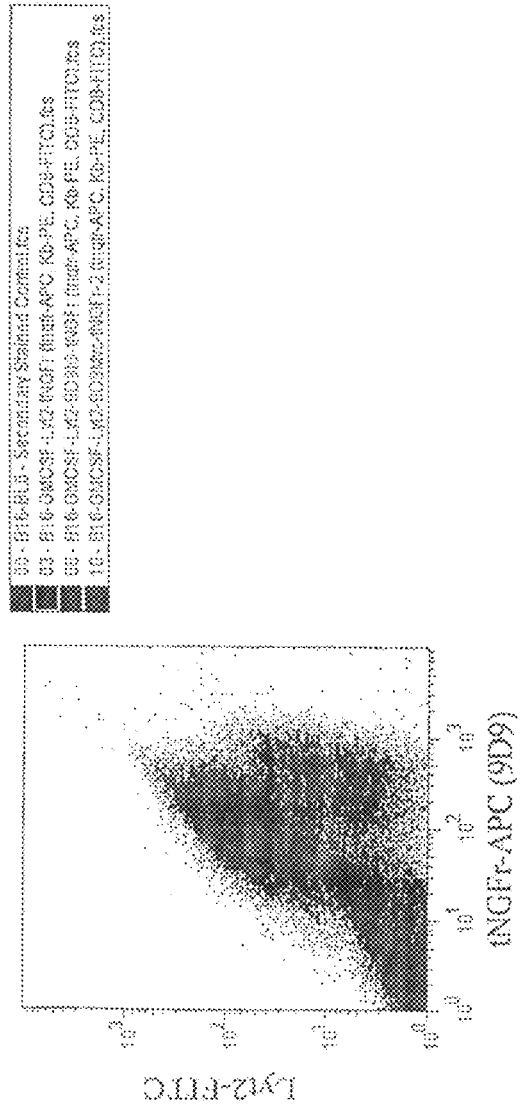
FIG. 10 depicts CD spectra of B16-GM-transduced with 9D9scFv.

FIG. 10 depicts CD spectra of B16-GM-9D9scFv tranduced cell lines.

Example 6

The anti-CTLA-4 scFv molecules and monoclonal antibodies were transduced into B16 cells and used to treat tumors. Animals were grouped and treated as follows:

TABLE 1

Group 1: PBS
Group 2: B16-GMCSF-tNGFr
Group 3: B16-GM + 9D9 mAb
Group 4: B16-GM + 9D9 mAb + PC61

TABLE 1-continued

Group 5: B16-GM-9D9scFv-MycHis
Group 6: B16-GM-9D9scFv-Ig
Group 7: B16-GM-9D9scFv-MycHis + PC61
Group 8: B16-GM-9D9scFv-Ig + PC61

Mice were challenge with 15,000 B16-BL6 cells in growth-factor depleted matrigel (BD) sub-cutaneously on the right flank and on the same day vaccinated with 1,000,000 irradiated B16-GMCSF cells sub-cutaneously on the left flank. Mice received vaccine boosts on day 3 and day 6. Some mice were depleted of T-reg cells by i.p. injection of 350 ug of the PC-61 anti-CD25 antibody on Day-4. Some mice received 100 ug of the 9D9 anti-CTLA4 antibody i.p. on days 0, 3, and 6.

On Day 18 tumors were measured using calipers. Mice were then sacrificed and tumors were isolated. Tumors were dispersed by crushing with a syringe plunger followed by passage through a 70 um cell strainer and gradient purification using Ficoll.

Tumor cells were stained with anti-CD8 APC (Pharmingen) and FoxP3-PE (eBiosciences) using the eBiosciences FoxP3 staining kit following manufacturer's instructions. The CD8+ cell to FoxP3+ cell ration was calculated following flow cytometric analysis on a Cyan LX (Cytomation).

Figure 11:
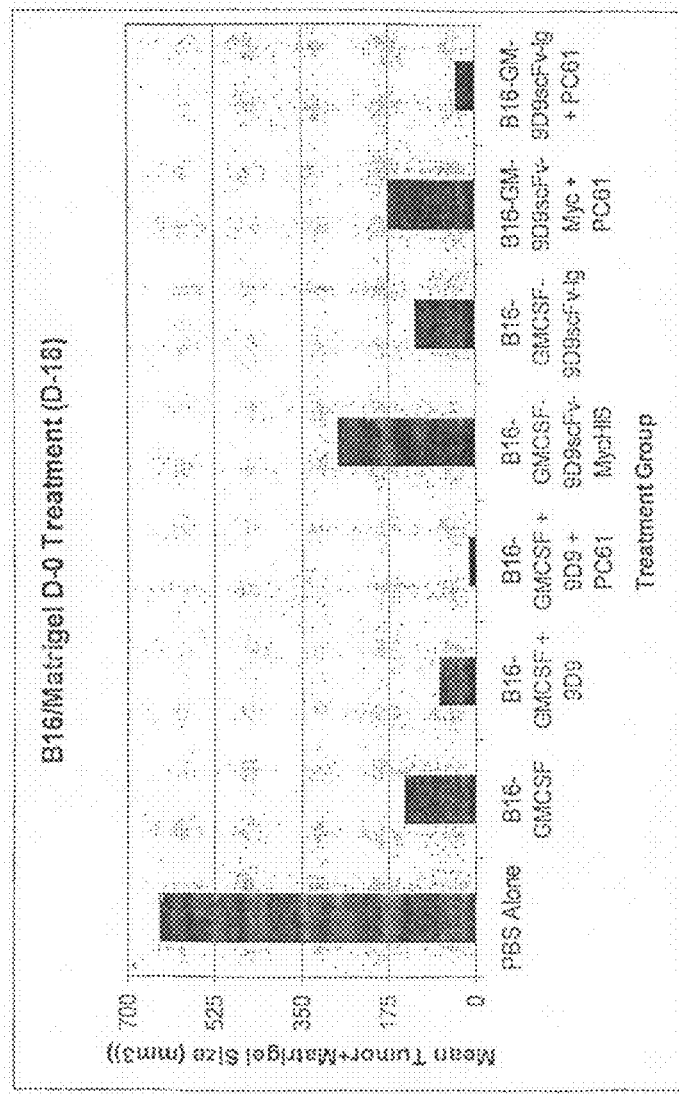
FIG. 11 depicts the tumor/matrigel size in mice 18 days after treatment with the shown anti-CTLA-4 monoclonal antibodies and scFv molecules.

FIG. 11 depicts Tumor/Matrigel Size mice 18 days after treatment with anti-CTLA-4 monoclonal antibodies and scFv molecules. FIG. 12 depicts the intra-tumor T-cell profile in mice 18 days after treatment with the shown anti-CTLA-4 monoclonal antibodies and scFv molecules. The B16-GM-CSF-909 cells showed reduced tumor size and increased CD8+ proliferation as compared to B16-GM-CSF cells.

The 9D9 anti-CTLA4 scFv was tailed with a mouse IgG1 antibody constant region in which the hinge cysteines were changed to serines to prevent dimerization and to reduce Fc-receptor binding. This variant of the scFv bound CTLA-4 and should be able to block its interaction with B7 (the constant region helps stabilize binding and provides additional bulk for blockade). Low Fc-receptor binding reduces the chance of the scFv being bound on the surface of APCs where it could cross-link CTLA4 on the surface of T-cells and send a negative signal.

Two other scFv molecules which bind to CTLA4 exert a primarily immunosuppressive effect. Without being limited to a specific mechanism of action, the cMyc and 6XH1S epitope tag (set forth as SEQ ID NO:1) appeared to have a tolerizing effect. This form of the scFv may lack sufficient bulk to prevent B7-binding (i.e. it lacks the ability to prevent negative signaling), although it may also promote CTLA-4 cross-linking and tolerance of target T-cells. One potential explanation for this effect is that 9D9 scFv-MycHIS bound to CTLA4 on the surface of T-cells may then be bound by host antibody which recognizes the immunologically foreign tag in the tail. Binding of this host antibody to the scFv may result in indirect cross-linking of the CTLA4 molecules to which the scFv is bound sending a negative signal to the T-cell. These results suggest alternative embodiments of localized anti-CTLA antibody secretion having utility in immune suppression, such as transplantation and autoimmunity.

Example 7

The 9D9 scFv-IgG1 (Cys→Ser) was cloned into the pSFV1 vector or an enhanced SFV vector pSFVC2A. Full length vector RNA was produced in vitro using the SP6 Message Machine Kit (Ambion). SFV-9D9scFvIg RNA was electroporated into BHK cells using the Amaxa Cell Line Transfection Kit L (Amaxa). 24 Hours post-transfection RNA was purified from the BHK cells using Tri-Reagent (Sigma). cDNA was produced from this RNA using the Superscript II RT-PCR kit (Invitrogen). This cDNA was then analyzed for expression of the 9D9 scFv using PCR.

FIG. 13 depicts DT230 staining of B16-GM-9D9scFv Ig cell lines with DT230 raw supernatant and anti-mouse PE. Increased staining was observed for the 9D9 antibody, while an order of magnitude lower staining was observed for scFv 3B1 molecule.

Example 8

The 9D9 scFv anti-CTLA-4 antibody was administered to mice as described in Example 6.

Figure 14:
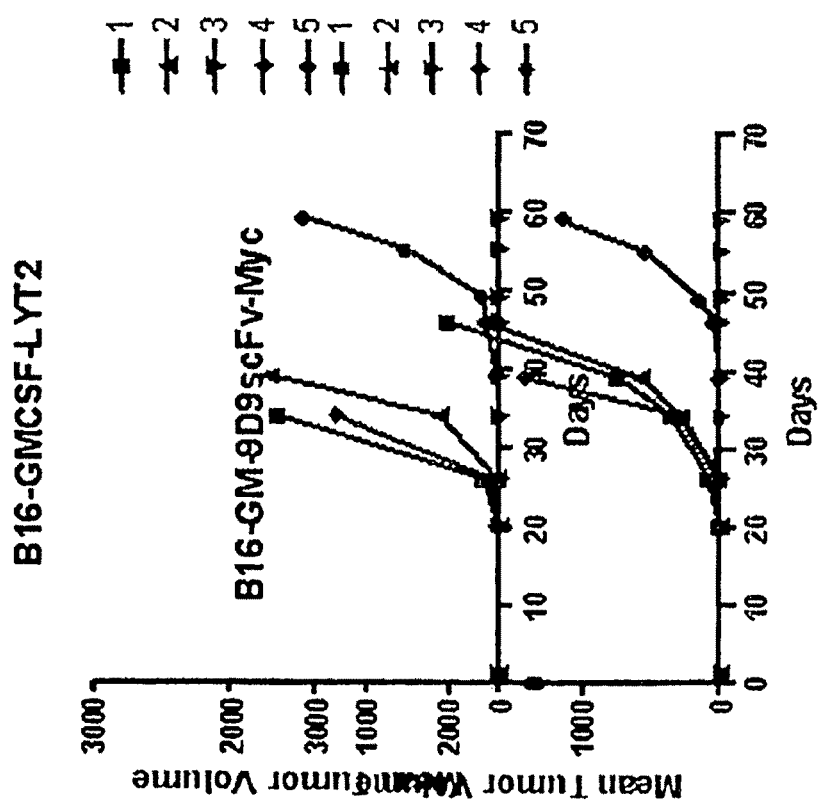
FIG. 14 depicts the delivery of the scFv anti-CTLA antibody at the site of tumor cell vaccine.

FIG. 14 depicts the mean tumor growth as a function of time after delivery of the scFv anti-CTLA antibody at the site of tumor cell vaccine. The tumor growth was delayed by a 3-6 days. These data suggests that systemic administration of the human cell (as opposed to localized administration) acts as a sustained release administration of the antibody. Antibody is produced by the cells while they remain alive, before the production of the antibodies slows and the cells begin to die.

We claim:

1. A viral vector comprising a nucleic acid encoding an anti-CTLA-4 antibody that binds to the extracellular domain of CTLA-4 and inhibits CTLA-4 signaling; wherein said antibody comprises all or part of an Fc region; and wherein said antibody comprises a variant hinge region lacking a cysteine residue capable of forming a disulphide linkage and exhibits reduced effector function.

2. The vector according to claim 1, further comprising a nucleic acid encoding a cytokine.

3. The vector according to claim 2, wherein said cytokine is GM-CSF.

4. The vector according to claim 1, wherein said anti-CTLA-4 antibody further comprises an scFv fragment.

5. The vector according to claim 1, wherein said anti-CTLA-4 antibody demonstrates reduced binding to Fc receptors.

6. The vector according to claim 1, wherein said viral vector is an integrative viral vector capable of providing constitutive expression when transfected into a human cell.

7. The vector according to claim 6, wherein said viral vector is selected from the group consisting of a retroviral vector, an adeno-associated viral (AAV) vector, and a lentiviral vector.

8. The vector according to claim 1, wherein said viral vector is a non-integrative viral vector capable of providing transient expression when transfected into a human cell.

9. The vector according to claim 8, wherein said vector is an alpha virus vector selected from the group consisting of an adenoviral vector and an alpha virus vector.

10. The vector according to claim 9, wherein said alpha virus vector is an SFV vector or a VEE vector.

11. A method of expressing an anti-CTLA-4 antibody proximal to a tumor cell in a patient comprising administering to said patient the vector according to any one of claims 1-4 and 6-10, wherein expression of said anti-CTLA-4 antibody inhibits CTLA-4 mediated negative signaling in T cells proximal to said tumor cell.

12. The method of claim 11, wherein said vector is non-integrative viral vector capable of providing transient expression when transfected into a human cell.

13. The method of claim 12, wherein said vector is administered proximal to said tumor cell.

14. The method of claim 12, wherein said vector is administered to a lymph node of the patient proximal to said tumor cell.

\* \* \* \* \*